US010329330B2

(12) United States Patent
Franken et al.

(10) Patent No.: US 10,329,330 B2
(45) Date of Patent: Jun. 25, 2019

(54) JC POLYOMAVIRUS VLP (VIRUS-LIKE PARTICLE) WITH A TARGETING PEPTIDE

(71) Applicant: LIFE SCIENCE INKUBATOR GMBH, Bonn (DE)

(72) Inventors: Sebastian Franken, Bonn (DE); Alexander Glassmann, Cologne (DE); Nadine Temme, Bonn (DE)

(73) Assignee: LIFE SCIENCE INKUBATOR GMBH, Bonn (DE)

( * ) Notice: Subject to any disclaimer, the term of this patent is extended or adjusted under 35 U.S.C. 154(b) by 0 days.

(21) Appl. No.: 15/533,377

(22) PCT Filed: Dec. 8, 2015

(86) PCT No.: PCT/EP2015/002466
§ 371 (c)(1),
(2) Date: Jun. 6, 2017

(87) PCT Pub. No.: WO2016/091375
PCT Pub. Date: Jun. 16, 2016

(65) Prior Publication Data
US 2018/0002384 A1 Jan. 4, 2018

(30) Foreign Application Priority Data

Dec. 8, 2014 (EP) .................................... 14196845

(51) Int. Cl.

| | |
|---|---|
| *C07K 14/01* | (2006.01) |
| *C07K 14/005* | (2006.01) |
| *C12N 7/04* | (2006.01) |
| *C07K 2/00* | (2006.01) |

(52) U.S. Cl.

CPC ................ *C07K 14/01* (2013.01); *C07K 2/00* (2013.01); *C07K 14/005* (2013.01); *C12N 7/04* (2013.01); *C07K 2319/01* (2013.01); *C12N 2710/22022* (2013.01); *C12N 2710/22023* (2013.01); *C12N 2710/22042* (2013.01); *C12N 2810/40* (2013.01)

(58) Field of Classification Search

CPC .................. C07K 14/005; C07K 14/01; C12N 2710/22023; C12N 2710/22042; C12N 2320/32; C12N 2810/40

See application file for complete search history.

(56) References Cited

U.S. PATENT DOCUMENTS

| | | | |
|---|---|---|---|
| 6,238,859 | B1 | 5/2001 | Lüke et al. |
| 2003/0044961 | A1 | 3/2003 | Luke et al. |
| 2004/0058316 | A1 | 3/2004 | Jensen et al. |
| 2004/0072180 | A1 | 4/2004 | Kappel et al. |
| 2006/0088936 | A1 | 4/2006 | Warrington et al. |
| 2006/0216238 | A1 | 9/2006 | Manchester et al. |
| 2010/0322862 | A1 | 12/2010 | Ruoslahti et al. |
| 2014/0309408 | A1 | 10/2014 | Demina et al. |
| 2015/0045417 | A1 | 2/2015 | Demina et al. |
| 2015/0297742 | A1 | 10/2015 | Strieker et al. |

FOREIGN PATENT DOCUMENTS

| | | | |
|---|---|---|---|
| DE | 600 37 263 | T2 | 10/2008 |
| EP | 1 219 705 | A1 | 7/2002 |
| EP | 1 270 586 | B1 | 11/2006 |
| EP | 2 554 664 | A1 | 2/2013 |
| EP | 2 636 746 | A1 | 9/2013 |
| EP | 2 774 991 | A1 | 9/2014 |
| WO | WO 97/19174 | A1 | 5/1997 |
| WO | WO 02/16424 | A2 | 2/2002 |
| WO | WO 2006/093967 | A2 | 9/2006 |
| WO | WO 2014/086835 | A1 | 6/2014 |

OTHER PUBLICATIONS

S. Gleiter et al.: "Changing the surface of a virus shell fusion of an enzyme to polyoma VP1", Protein Science, vol. 8, pp. 2562-2569 (1999).
S. Gleiter et al.: "Coupling of antibodies via protein Z on modified polyoma virus-like particles", Protein Science, vol. 10, pp. 434-444 (2001).
T. T. T. Vu et al.: "Soluble prokaryotic expression and purification of crotamine using an N-terminal maltose-binding protein tag", Toxicon, vol. 92, pp. 157-165 (2014).
E. A. Teunissen et al.: "Production and biomedical applications of virus-like particles derived from polyomaviruses", Journal of Controlled Release, vol. 172, pp. 305-321 (2013).
M. Högbom et al.: "Structural basis for recognition by an in vitro evolved affibody", PNAS, vol. 100, No. 6, pp. 3191-3196 (2003).
V. Fadel et al.: "Automated NMR structure determination and disulfide bond identification of the myotoxin crotamine from *Crotalus durissus* terrificus", Toxicon, vol. 46, pp. 759-767 (2005).
S. B. Needleman et al.: "A General Method Applicable to the Search for Similarities in the Amino Acid Sequence of Two Proteins", J. Mol. Biol., vol. 48, pp. 443-453 (1970).
P. Rice et al.: "EMBOSS: The European Molecular Biology Open Software Suite", TIG, vol. 16, No. 6, pp. 276-277 (2000).

(Continued)

*Primary Examiner* — Bao Q Li
(74) *Attorney, Agent, or Firm* — Norman B. Thot

(57) ABSTRACT

The disclosure relates to a fusion protein comprising at least a first and a second peptide, wherein —the second peptide comprises a targeting region and a first and a second interaction region, —the second peptide is located on the surface of the fusion protein; —the second peptide comprises at least two interaction pairs, wherein an interaction pair is formed by an amino acid of the first interaction region and an amino acid of the second interaction region, —the interaction between the amino acids of an interaction pair is covalent or non-covalent; and —at least one interaction pair is a covalent interaction pair in which the amino acids are covalently bound, and to virus like particles (VLP) comprising the fusion protein for use as drug delivery system. Also provided are polynucleotides encoding the fusion protein, suitable expression vectors, host cells, production methods for the fusion protein and the VLP comprising the fusion protein.

16 Claims, 6 Drawing Sheets

Specification includes a Sequence Listing.

(56) References Cited

OTHER PUBLICATIONS

Figures 1A, 1B:
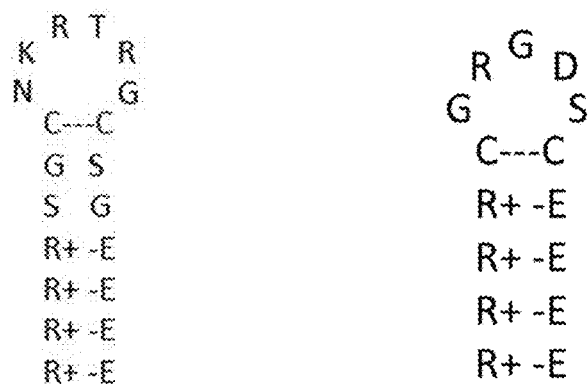
Figure 2:
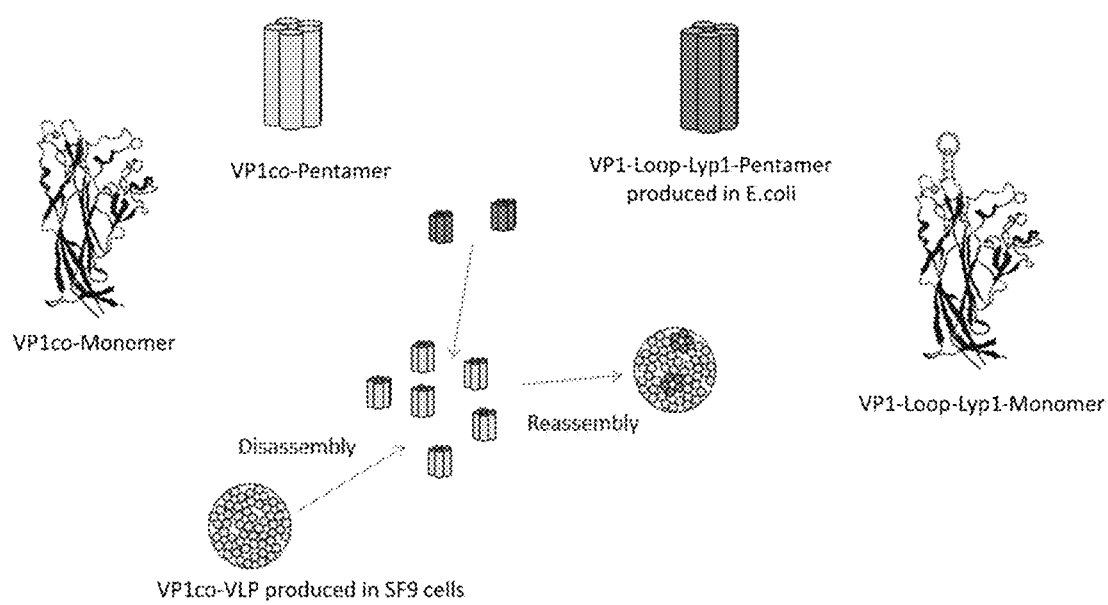
Figure 3:
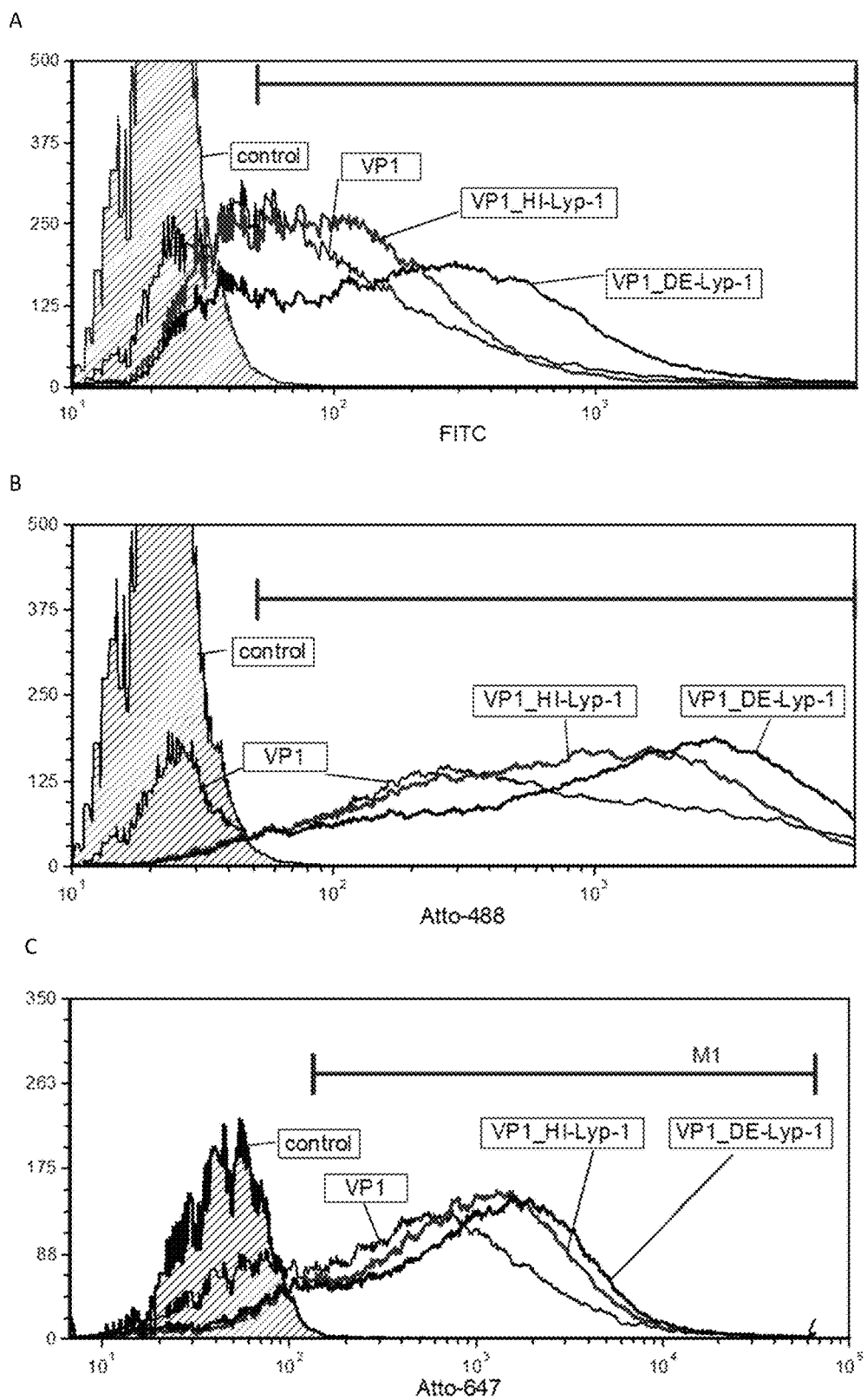
Figure 4:
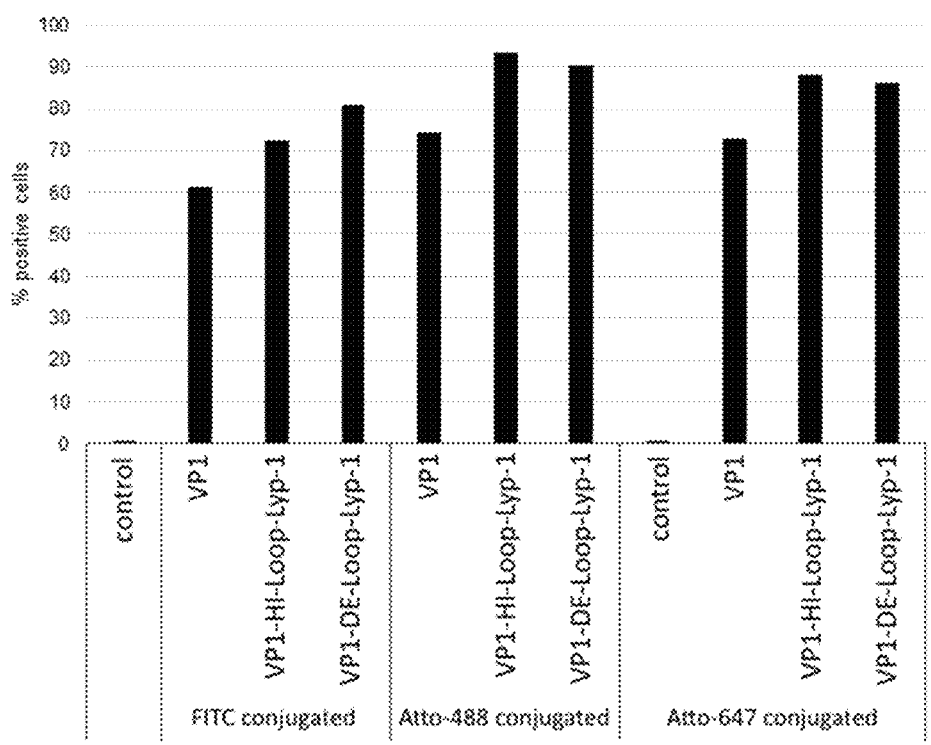

D. B. Troy: Remington: The Science and Practice of Pharmacy, 21$^{st}$ Edition, pp. 745-775, 802-836 and 837-849 (2006).

D. Simberg et al.: "Biomimetic amplification of nanoparticle homing to tumors", PNAS, vol. 104, No. 3, pp. 932-936 (2007).

E. Kondo et al.: "Tumour lineage-homing cell-penetrating peptides as anticancer molecular delivery systems", nature communications, vol. 3, No. 951, pp. 1-13 (2012).

S. Christian et al.: "Nucleolin expressed at the cell surface is a marker of endothelial cells in angiogenic blood vessels", The Journal of Cell Biology, vol. 163, No. 4, pp. 871-878 (2003).

K. Hajdin et al.: "Furin Targeted Drug Delivery for Treatment of Rhabdomyosarcoma in a Mouse Model", PLoS One, vol. 5, No. 5, pp. 1-13 (2010).

T. P. Herringson et al.: "Effective tumor targeting and enhanced anti-tumor effect of liposomes engrafted with peptides specific for tumor lymphatics and vasculature", International Journal of Pharmaceutics, vol. 411, pp. 206-214 (2011).

M. Shadidi et al.: "Identification of novel carrier peptides for the specific delivery of therapeutics into cancer cells", The FASEB Journal, vol. 17, No. 2, pp. 1-17 (2003).

D.-K. Chang et al.: "A Novel Peptide Enhances Therapeutic Efficacy of Liposomal Anti-Cancer Drugs in Mice Models of Human Lung Cancer", PLoS One, vol. 4, No. 1, pp. 1-11 (2009).

M. A. Innis et al.: "PCR Protocols: A Guide to Methods and Applications", Academic Press, Inc., pp. 1-9 (1990).

J. Sambrook et al.: "Molecular Cloning: A Laboratory Manual", Second Edition, Summary, pp. 1-2 (1989).

J.-C. Janson et al.: "Protein Purification: Principles, High Resolution Methods, and Applications", Wiley-VCH, Second Edition, pp. 1-6 (1998).

E. Boura et al.: "Polyomavirus EGFP-pseudocapsids: Analysis of model particles for introduction of proteins and peptides into mammalian cells", FEBS Letters, vol. 579, pp. 6549-6558 (2005).

K. Tegerstedt et al.: "Murine Polyomavirus Virus-Like Particles (VLPs) as Vectors for Gene and Immune Therapy and Vaccines against Viral Infections and Cancer", Anticancer Research, vol. 25, pp. 2601-2608 (2005).

A. Abbing et al.: "Efficient Intracellular Delivery of a Protein and a Low Molecular Weight Substance via Recombinant Polyomavirus-like Particles", The Journal of Biological Chemistry, vol. 279, No. 26, pp. 27410-27421 (2004).

J. Derouchey et al.: "A comparison of DNA compaction by arginine and lysine peptides: A physical basis for arginine rich protamines", Biochemistry, vol. 52, No. 17, pp. 1-24 (2013).

C. Bechara et al.: "Cell-penetrating peptides: 20 years later, where do we stand?", FEBS Letters, vol. 587, pp. 1693-1702 (2013).

Y. Pan et al.: "Development of a microRNA delivery system based on bacteriophage MS2 virus-like particles", FEBS Journal, vol. 279, No. 7, pp. 1198-1208 (2012).

B. Wei et al.: "Development of an antisense RNA delivery system using conjugates of the MS2 bacteriophage capsids and HIV-1 TAT cell penetrating peptide", Biomedicine & Pharmacotherapy, vol. 63, pp. 313-318 (2009).

P. Järver et al.: "In vivo biodistribution and efficacy of peptide mediated delivery", Trends in Pharmacological Sciences, vol. 31, No. 11, pp. 528-535, (2010).

D.-X. Ma et al.: "Distinct transduction modes of arginine-rich cell-penetrating peptides for cargo delivery into tumor cells", International Journal of Pharmaceutics, vol. 419, pp. 200-208 (2011).

S. Jagu et al.: "Vaccination with multimeric L2 fusion protein and L1 VLP or capsomeres to broaden protection against HPV infection", Vaccine, vol. 28, pp. 4478-4486 (2010).

N. Kämper et al.: "A Membrane-Destabilizing Peptide in Capsid Protein L2 is Required for Egress of Papillomavirus Genomes from Endosomes", Journal of Virology, pp. 759-768 (2006).

D. M. Hoover et al.: "The Structure of Human β-Defensin-1: New Insights Into Structural Properties of β-Defensins", The Journal of Biological Chemistry, vol. 276, No. 42, pp. 39021-39026 (2001).

SEQUENCE LISTING

```
<160> NUMBER OF SEQ ID NOS: 79

<210> SEQ ID NO 1
<211> LENGTH: 9
<212> TYPE: PRT
<213> ORGANISM: Artificial Sequence
<220> FEATURE:
<223> OTHER INFORMATION: Designed peptide

<400> SEQUENCE: 1

Cys Gly Asn Lys Arg Thr Arg Gly Cys
1               5

<210> SEQ ID NO 2
<211> LENGTH: 6
<212> TYPE: PRT
<213> ORGANISM: Artificial Sequence
<220> FEATURE:
<223> OTHER INFORMATION: Designe peptide

<400> SEQUENCE: 2

Lys Cys Cys Tyr Ser Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Designed peptide
```

```
<400> SEQUENCE: 3

Cys Arg Glu Lys Ala
1               5

<210> SEQ ID NO 4
<211> LENGTH: 15
<212> TYPE: PRT
<213> ORGANISM: Campylobacter spec.

<400> SEQUENCE: 4

Asp Ser Leu Lys Ser Tyr Trp Tyr Leu Gln Lys Phe Ser Trp Arg
1               5                   10                  15

<210> SEQ ID NO 5
<211> LENGTH: 15
<212> TYPE: PRT
<213> ORGANISM: Campylobacter spec.

<400> SEQUENCE: 5

Lys Arg Pro Thr Met Arg Phe Arg Tyr Thr Trp Asn Pro Met Lys
1               5                   10                  15

<210> SEQ ID NO 6
<211> LENGTH: 31
<212> TYPE: PRT
<213> ORGANISM: Homo sapiens (human)

<400> SEQUENCE: 6

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 7
<211> LENGTH: 12
<212> TYPE: PRT
<213> ORGANISM: Artificial Sequence
<220> FEATURE:
<223> OTHER INFORMATION: Designed peptide

<400> SEQUENCE: 7

Cys Met Gly Thr Ile Asn Thr Arg Thr Lys Lys Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Designed peptide

<400> SEQUENCE: 8

Trp His Ser Asp Met Glu Trp Trp Tyr Leu Leu Gly
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Designed peptide

<400> SEQUENCE: 9

Leu Thr Val Ser Pro Trp Tyr
```

<210> SEQ ID NO 10
<211> LENGTH: 12
<212> TYPE: PRT
<213> ORGANISM: Artificial Sequence
<220> FEATURE:
<223> OTHER INFORMATION: Designed peptide

<400> SEQUENCE: 10

Trp Asn Leu Pro Trp Tyr Tyr Ser Val Ser Pro Thr
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Designed peptide

<400> SEQUENCE: 11

Asn Gly Tyr Glu Ile Glu Trp Tyr Ser Trp Val Thr His Gly Met Tyr
1               5                   10                  15

<210> SEQ ID NO 12
<211> LENGTH: 611
<212> TYPE: PRT
<213> ORGANISM: JC-Polyomavirus

<400> SEQUENCE: 12

Met Ala Pro Thr Lys Arg Lys Gly Glu Pro Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu

```
            225                 230                 235                 240

Phe Gly Val Gly Pro Leu Cys Lys Gly Asp Asn Leu Tyr Leu Ser Ala
                        245                 250                 255

Val Asp Val Cys Gly Met Phe Thr Asn Gly Ser Gln Gln Trp Arg Gly
                        260                 265                 270

Leu Ser Arg Tyr Phe Lys Val Gln Leu Arg Lys Arg Val Lys Asn
                        275                 280                 285

Pro Tyr Pro Ile Ser Phe Leu Leu Thr Asp Leu Ile Asn Arg Arg Thr
                        290                 295                 300

Pro Arg Val Asp Gly Gln Pro Met Tyr Gly Met Asp Ala Gln Val Glu
        305                 310                 315                 320

Glu Val Arg Val Phe Glu Gly Thr Glu Glu Leu Pro Gly Asp Pro Asp
                        325                 330                 335

Met Met Arg Tyr Val Asp Lys Tyr Gly Gln Leu Gln Thr Lys Met Cys
                        340                 345                 350

Ile Thr Gly Asp Ala Leu Val Ala Leu Pro Glu Gly Glu Ser Val Arg
                        355                 360                 365

Ile Ala Asp Ile Val Pro Gly Ala Arg Pro Asn Ser Asp Asn Ala Ile
                        370                 375                 380

Asp Leu Lys Val Leu Asp Arg His Gly Asn Pro Val Leu Ala Asp Arg
        385                 390                 395                 400

Leu Phe His Ser Gly Glu His Pro Val Tyr Thr Val Arg Thr Val Glu
                        405                 410                 415

Gly Leu Arg Val Thr Gly Thr Ala Asn His Pro Leu Leu Cys Leu Val
                        420                 425                 430

Asp Val Ala Gly Val Pro Thr Leu Leu Trp Lys Leu Ile Asp Glu Ile
                        435                 440                 445

Lys Pro Gly Asp Tyr Ala Val Ile Gln Arg Ser Ala Phe Ser Val Asp
                        450                 455                 460

Cys Ala Gly Phe Ala Arg Gly Lys Pro Glu Phe Ala Pro Thr Thr Tyr
        465                 470                 475                 480

Thr Val Gly Val Pro Gly Leu Val Arg Phe Leu Glu Ala His His Arg
                        485                 490                 495

Asp Pro Asp Ala Gln Ala Ile Ala Asp Glu Leu Thr Asp Gly Arg Phe
                        500                 505                 510

Tyr Tyr Ala Lys Val Ala Ser Val Thr Asp Ala Gly Val Gln Pro Val
                        515                 520                 525

Tyr Ser Leu Arg Val Asp Thr Ala Asp His Ala Phe Ile Thr Asn Gly
                        530                 535                 540

Phe Val Ser His Ala Thr Gly Leu Thr Gly Leu Asn Ser Gly Leu Thr
        545                 550                 555                 560

Thr Asn Pro Gly Val Ser Ala Trp Gln Val Asn Thr Ala Tyr Thr Ala
                        565                 570                 575

Gly Gln Leu Val Thr Tyr Asn Gly Lys Thr Tyr Lys Cys Leu Gln Pro
                        580                 585                 590

His Thr Ser Leu Ala Gly Trp Glu Pro Ser Asn Val Pro Ala Leu Trp
                        595                 600                 605

Gln Leu Gln
            610

<210> SEQ ID NO 13
<211> LENGTH: 21
<212> TYPE: PRT
<213> ORGANISM: Artificial Sequence
```

<220> FEATURE:
<223> OTHER INFORMATION: Designed peptide

<400> SEQUENCE: 13

Arg Arg Arg Arg Ser Gly Cys Gly Asn Lys Arg Thr Arg Gly Cys Gly
1               5                   10                  15

Ser Glu Glu Glu Glu
            20

<210> SEQ ID NO 14
<211> LENGTH: 632
<212> TYPE: PRT
<213> ORGANISM: Artificial Sequence
<220> FEATURE:
<223> OTHER INFORMATION: Designed peptide

<400> SEQUENCE: 14

Met Ala Pro Thr Lys Arg Lys Gly Glu Pro Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Arg Arg Arg Arg Ser Gly Cys Gly Asn Lys Arg Thr Arg Gly Cys
    130                 135                 140

Gly Ser Glu Glu Glu Glu Gly Ala Gly Lys Pro Val Gln Gly Thr Ser
145                 150                 155                 160

Phe His Phe Phe Ser Val Gly Gly Glu Ala Leu Glu Leu Gln Gly Val
                165                 170                 175

Val Phe Asn Tyr Arg Thr Lys Tyr Pro Asp Gly Thr Ile Phe Pro Lys
            180                 185                 190

Asn Ala Thr Val Gln Ser Gln Val Met Asn Thr Glu His Lys Ala Tyr
        195                 200                 205

Leu Asp Lys Asn Lys Ala Tyr Pro Val Glu Cys Trp Val Pro Asp Pro
    210                 215                 220

Thr Arg Asn Glu Asn Thr Arg Tyr Phe Gly Thr Leu Thr Gly Gly Glu
225                 230                 235                 240

Asn Val Pro Pro Val Leu His Ile Thr Asn Thr Ala Thr Thr Val Leu
                245                 250                 255

Leu Asp Glu Phe Gly Val Gly Pro Leu Cys Lys Gly Asp Asn Leu Tyr
            260                 265                 270

Leu Ser Ala Val Asp Val Cys Gly Met Phe Thr Asn Arg Ser Gly Ser
        275                 280                 285

Gln Gln Trp Arg Gly Leu Ser Arg Tyr Phe Lys Val Gln Leu Arg Lys
    290                 295                 300

Arg Arg Val Lys Asn Pro Tyr Pro Ile Ser Phe Leu Leu Thr Asp Leu

```
              305                 310                 315                 320
        Ile Asn Arg Arg Thr Pro Arg Val Asp Gly Gln Pro Met Tyr Gly Met
                            325                 330                 335

Asp Ala Gln Val Glu Glu Val Arg Val Phe Glu Gly Thr Glu Glu Leu
                            340                 345                 350

Pro Gly Asp Pro Asp Met Met Arg Tyr Val Asp Lys Tyr Gly Gln Leu
                            355                 360                 365

Gln Thr Lys Met Cys Ile Thr Gly Asp Ala Leu Val Ala Leu Pro Glu
                    370                 375                 380

Gly Glu Ser Val Arg Ile Ala Asp Ile Val Pro Gly Ala Arg Pro Asn
        385                 390                 395                 400

Ser Asp Asn Ala Ile Asp Leu Lys Val Leu Asp Arg His Gly Asn Pro
                            405                 410                 415

Val Leu Ala Asp Arg Leu Phe His Ser Gly Glu His Pro Val Tyr Thr
                            420                 425                 430

Val Arg Thr Val Glu Gly Leu Arg Val Thr Gly Thr Ala Asn His Pro
                    435                 440                 445

Leu Leu Cys Leu Val Asp Val Ala Gly Val Pro Thr Leu Leu Trp Lys
                    450                 455                 460

Leu Ile Asp Glu Ile Lys Pro Gly Asp Tyr Ala Val Ile Gln Arg Ser
        465                 470                 475                 480

Ala Phe Ser Val Asp Cys Ala Gly Phe Ala Arg Gly Lys Pro Glu Phe
                            485                 490                 495

Ala Pro Thr Thr Tyr Thr Val Gly Val Pro Gly Leu Val Arg Phe Leu
                            500                 505                 510

Glu Ala His His Arg Asp Pro Asp Ala Gln Ala Ile Ala Asp Glu Leu
                            515                 520                 525

Thr Asp Gly Arg Phe Tyr Tyr Ala Lys Val Ala Ser Val Thr Asp Ala
                    530                 535                 540

Gly Val Gln Pro Val Tyr Ser Leu Arg Val Asp Thr Ala Asp His Ala
        545                 550                 555                 560

Phe Ile Thr Asn Gly Phe Val Ser His Ala Thr Gly Leu Thr Gly Leu
                            565                 570                 575

Asn Ser Gly Leu Thr Thr Asn Pro Gly Val Ser Ala Trp Gln Val Asn
                            580                 585                 590

Thr Ala Tyr Thr Ala Gly Gln Leu Val Thr Tyr Asn Gly Lys Thr Tyr
                    595                 600                 605

Lys Cys Leu Gln Pro His Thr Ser Leu Ala Gly Trp Glu Pro Ser Asn
                    610                 615                 620

Val Pro Ala Leu Trp Gln Leu Gln
        625                 630

<210> SEQ ID NO 15
<211> LENGTH: 632
<212> TYPE: PRT
<213> ORGANISM: Artificial Sequence
<220> FEATURE:
<223> OTHER INFORMATION: Designed peptide

<400> SEQUENCE: 15

Met Ala Pro Thr Lys Arg Lys Gly Glu Pro Lys Asp Pro Val Gln Val
        1               5                   10                  15

Pro Lys Leu Leu Ile Arg Gly Gly Val Glu Val Leu Glu Val Lys Thr
                    20                  25                  30

Gly Val Asp Ser Ile Thr Glu Val Glu Cys Phe Leu Thr Pro Glu Met
```

```
                35                  40                  45
Gly Asp Pro Asp Glu His Leu Arg Gly Phe Ser Lys Ser Ile Ser Ile
 50                  55                  60

Ser Asp Thr Phe Glu Ser Asp Ser Pro Asn Arg Asp Met Leu Pro Cys
 65                  70                  75                  80

Tyr Ser Val Ala Arg Ile Pro Leu Pro Asn Leu Asn Glu Asp Leu Thr
                 85                  90                  95

Cys Gly Asn Ile Leu Met Trp Glu Ala Val Thr Leu Lys Thr Glu Val
                100                 105                 110

Ile Gly Val Thr Ser Leu Met Asn Val His Ser Asn Gly Gln Ala Thr
                115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
                180                 185                 190

Asn Lys Ala Tyr Pro Val Glu Cys Trp Val Pro Asp Pro Thr Arg Asn
                195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Arg Arg Ser Gly Cys
                260                 265                 270

Gly Asn Lys Arg Thr Arg Gly Cys Gly Ser Glu Glu Glu Gly Ser
                275                 280                 285

Gln Gln Trp Arg Gly Leu Ser Arg Tyr Phe Lys Val Gln Leu Arg Lys
290                 295                 300

Arg Arg Val Lys Asn Pro Tyr Pro Ile Ser Phe Leu Leu Thr Asp Leu
305                 310                 315                 320

Ile Asn Arg Arg Thr Pro Arg Val Asp Gly Gln Pro Met Tyr Gly Met
                325                 330                 335

Asp Ala Gln Val Glu Glu Val Arg Val Phe Glu Gly Thr Glu Glu Leu
                340                 345                 350

Pro Gly Asp Pro Asp Met Met Arg Tyr Val Asp Lys Tyr Gly Gln Leu
                355                 360                 365

Gln Thr Lys Met Cys Ile Thr Gly Asp Ala Leu Val Ala Leu Pro Glu
                370                 375                 380

Gly Glu Ser Val Arg Ile Ala Asp Ile Val Pro Gly Ala Arg Pro Asn
385                 390                 395                 400

Ser Asp Asn Ala Ile Asp Leu Lys Val Leu Asp Arg His Gly Asn Pro
                405                 410                 415

Val Leu Ala Asp Arg Leu Phe His Ser Gly Glu His Pro Val Tyr Thr
                420                 425                 430

Val Arg Thr Val Glu Gly Leu Arg Val Thr Gly Thr Ala Asn His Pro
                435                 440                 445

Leu Leu Cys Leu Val Asp Val Ala Gly Val Pro Thr Leu Leu Trp Lys
450                 455                 460
```

Leu Ile Asp Glu Ile Lys Pro Gly Asp Tyr Ala Val Ile Gln Arg Ser
465                 470                 475                 480

Ala Phe Ser Val Asp Cys Ala Gly Phe Ala Arg Gly Lys Pro Glu Phe
            485                 490                 495

Ala Pro Thr Thr Tyr Thr Val Gly Val Pro Gly Leu Val Arg Phe Leu
            500                 505                 510

Glu Ala His His Arg Asp Pro Asp Ala Gln Ala Ile Ala Asp Glu Leu
        515                 520                 525

Thr Asp Gly Arg Phe Tyr Tyr Ala Lys Val Ala Ser Val Thr Asp Ala
    530                 535                 540

Gly Val Gln Pro Val Tyr Ser Leu Arg Val Asp Thr Ala Asp His Ala
545                 550                 555                 560

Phe Ile Thr Asn Gly Phe Val Ser His Ala Thr Gly Leu Thr Gly Leu
                565                 570                 575

Asn Ser Gly Leu Thr Thr Asn Pro Gly Val Ser Ala Trp Gln Val Asn
            580                 585                 590

Thr Ala Tyr Thr Ala Gly Gln Leu Val Thr Tyr Asn Gly Lys Thr Tyr
        595                 600                 605

Lys Cys Leu Gln Pro His Thr Ser Leu Ala Gly Trp Glu Pro Ser Asn
    610                 615                 620

Val Pro Ala Leu Trp Gln Leu Gln
625                 630

<210> SEQ ID NO 16
<211> LENGTH: 1065
<212> TYPE: DNA
<213> ORGANISM: JC-Polyomavirus

<400> SEQUENCE: 16

```
atggctccca ccaagcgcaa gggcgagccc aaggaccccg tgcaagtgcc caagctgctg      60
atccgtggtg gtgtcgaggt gctggaagtc aagaccggcg tggactccat taccgaggtg     120
gagtgcttcc tcaccccga  tgggtgac   cctgacgagc acctgagggg cttctccaag     180
tccatctcca tctccgacac cttcgagtcc gactccccca accgtgacat gctgccctgc     240
tactccgtgg ctcgtatccc cctgcccaac ctgaacgagg acctgacttg cggcaacatc     300
ctgatgtggg aggctgtgac cctcaagacc gaggtcatcg gcgtgacttc cctgatgaac     360
gtgcactcca acggccaggc tacccacgac aacggtgctg gcaagcccgt gcagggaacc     420
tccttccact tcttctccgt gggtggcgag gctctggaac tccagggcgt ggtgttcaac     480
taccgtacca agtaccccga cggcaccatc ttccccaaga cgctactgt  gcagtcccaa     540
gtgatgaaca ccgagcacaa ggcttacctg gacaagaaca aggcctaccc cgtggagtgc     600
tgggtgcccg accccacccg taacgagaac accgttact  tcggcaccct gaccggtgga     660
gagaacgtgc ccccgtgct  gcacatcacc aacaccgcta ccaccgtgct gctggacgag     720
ttcggtgtcg gtcccctgtg caagggcgac aacctgtacc tgtccgctgt ggacgtgtgc     780
ggcatgttca ccaaccgttc cggttcccag cagtggcgtg gcctgtcccg ctacttcaag     840
gtgcagctgc gcaagcgtcg tgtgaagaac ccctacccta tctccttcct gctgaccgac     900
ctgatcaacc gtcgtacccc tcgtgtggac ggccagccca tgtacggcat ggacgctcag     960
gtggaagagg tccgcgtgtt cgagggcacc gaggaattgc ccggcgaccc cgacatgatg    1020
cgttacgtgg acaagtacgg ccagctccag accaagatgc tgtaa                    1065
```

```
<210> SEQ ID NO 17
<211> LENGTH: 63
<212> TYPE: DNA
<213> ORGANISM: Artificial Sequence
<220> FEATURE:
<223> OTHER INFORMATION: Gene sequence of designed peptide

<400> SEQUENCE: 17
cgtagacgta gatcaggttg tggtaacaag cgaactagag ggtgcggatc cgaagaggaa      60
gag                                                                   63

<210> SEQ ID NO 18
<211> LENGTH: 1899
<212> TYPE: DNA
<213> ORGANISM: Artificial Sequence
<220> FEATURE:
<223> OTHER INFORMATION: Gene sequence of designed peptide

<400> SEQUENCE: 18
atggctccca ccaagcgcaa gggcgagccc aaggaccccg tgcaagtgcc caagctgctg      60
atccgtggtg gtgtcgaggt gctggaagtc aagaccggcg tggactccat taccgaggtg     120
gagtgcttcc tcaccccga gatgggtgac cctgacgagc acctgagggg cttctccaag     180
tccatctcca tctccgacac cttcgagtcc gactccccca accgtgacat gctgccctgc     240
tactccgtgg ctcgtatccc cctgcccaac ctgaacgagg acctgacttg cggcaacatc     300
ctgatgtggg aggctgtgac cctcaagacc gaggtcatcg gcgtgacttc cctgatgaac     360
gtgcactcca acggccaggc tacccaccgt agacgtagat caggttgtgg taacaagcga     420
actagagggt gcggatccga agaggaagag ggtgctggca gcccgtgca gggaacctcc     480 ttccacttct tctccgtggg tggcgaggct ctggaactcc agggcgtggt gttcaactac     540
cgtaccaagt accccgacgg caccatcttc cccaagaacg ctactgtgca gtcccaagtg     600
atgaacaccg agcacaaggc ttacctggac aagaacaagg cctacccgt ggagtgctgg     660 gtgcccgacc ccaccgtaa cgagaacacc cgttacttcg gcaccctgac cggtggagag     720
aacgtgcccc ccgtgctgca catcaccaac accgctacca ccgtgctgct ggacgagttc     780
ggtgtcggtc cctgtgcaa gggcgacaac ctgtacctgt ccgctgtgga cgtgtgcggc     840
atgttcacca accgttccgg ttcccagcag tggcgtggcc tgtcccgcta cttcaaggtg     900
cagctgcgca agcgtcgtgt gaagaacccc taccctatct ccttcctgct gaccgacctg     960
atcaaccgtc gtacccctcg tgtggacggc cagcccatgt acggcatgga cgctcaggtg    1020
gaagaggtcc gcgtgttcga gggcaccgag gaattgcccg cgaccccga catgatgcgt    1080 tacgtggaca gtacggcca gctccagacc aagatgtgca tcacgggaga tgcactagtt    1140
gccctacccg agggcgagtc ggtacgcatc gccgacatcg tgccgggtgc gcggcccaac    1200
agtgacaacg ccatcgacct gaaagtcctt gaccggcatg gcaatcccgt gctcgccgac    1260
cggctgttcc actccggcga gcatccggtg tacacggtgc gtacggtcga aggtctgcgt    1320
gtgacgggca ccgcgaacca cccgttgttg tgtttggtcg acgtcgccgg ggtgccgacc    1380
ctgctgtgga gctgatcga cgaaatcaag ccgggcgatt acgcggtgat tcaacgcagc    1440
gcattcagcg tcgactgtgc aggttttgcc cgcgggaaac ccgaatttgc gcccacaacc    1500
tacacagtcg gcgtccctgg actggtgcgt ttcttggaag cacaccaccg agacccggac    1560
gcccaagcta tcgccgacga gctgaccgac gggcggttct actacgcgaa agtcgccagt    1620
gtcaccgacg ccggcgtgca gccggtgtat agccttcgtg tcgacacggc agaccacgcg    1680
```

```
tttatcacga acgggttcgt cagccacgct actggcctca ccggtctgaa ctcaggcctc    1740
acgacaaatc ctggtgtatc cgcttggcag gtcaacacag cttatactgc gggacaattg    1800
gtcacatata acggcaagac gtataaatgt ttgcagcccc acacctcctt ggcaggatgg    1860
gaaccatcca acgttcctgc cttgtggcag cttcaatga                           1899
```

<210> SEQ ID NO 19
<211> LENGTH: 1899
<212> TYPE: DNA
<213> ORGANISM: Artificial Sequence
<220> FEATURE:
<223> OTHER INFORMATION: Gene sequence of designed peptide

<400> SEQUENCE: 19

```
atggctccca ccaagcgcaa gggcgagccc aaggaccccg tgcaagtgcc caagctgctg     60
atccgtggtg gtgtcgaggt gctggaagtc aagaccggcg tggactccat taccgaggtg    120
gagtgcttcc tcaccccga gatgggtgac cctgacgagc acctgagggg ctttctccaag   180 tccatctcca tctccgacac cttcgagtcc gactccccca ccgtgacat gctgccctgc    240 tactccgtgg ctcgtatccc cctgcccaac ctgaacgagg acctgacttg cggcaacatc    300
ctgatgtggg aggctgtgac cctcaagacc gaggtcatcg gcgtgacttc cctgatgaac    360
gtgcactcca acggccaggc tacccacgac aacggtgctg gcaagcccgt gcagggaacc    420
tccttccact tcttctccgt gggtggcgag gctctggaac tccagggcgt ggtgttcaac    480
taccgtacca agtaccccga cggcaccatc ttccccaaga cgctactgt gcagtcccaa    540 gtgatgaaca ccgagcacaa ggcttacctg gacaagaaca aggcctaccc cgtggagtgc    600
tgggtgcccg accccacccg taacgagaac accgttact tcggcaccct gaccggtgga    660
gagaacgtgc ccccgtgct gcacatcacc aacaccgcta ccaccgtgct gctggacgag    720
ttcggtgtcg gtccctgtg caagggcgac aacctgtacc tgtccgctgt ggacgtgtgc    780
ggcatgttca ccaaccgtag acgtagatca ggttgtggta acaagcgaac tagagggtgc    840
ggatccgaag aggaagaggg ttcccagcag tggcgtggcc tgtcccgcta cttcaaggtg    900
cagctgcgca agcgtcgtgt gaagaacccc taccctatct ccttcctgct gaccgacctg    960
atcaaccgtc gtacccctcg tgtggacggc cagcccatgt acggcatgga cgctcaggtg    1020
gaagaggtcc gcgtgttcga gggcaccgag gaattgcccg cgaccccga catgatgcgt    1080 tacgtggaca agtacggcca gctccagacc aagatgtgca tcacgggaga tgcactagtt    1140
gccctacccg agggcgagtc ggtacgcatc gccgacatcg tgccgggtgc gcggcccaac    1200
agtgacaacg ccatcgacct gaaagtcctt gaccggcatg gcaatcccgt gctcgccgac    1260
cggctgttcc actccggcga gcatccggta tacgcggtgc gtacggtcga aggtctgcgt    1320
gtgacgggca ccgcgaacca cccgttgttg tgtttggtcg acgtcgccgg ggtgccgacc    1380
ctgctgtgga agctgatcga cgaaatcaag ccgggcgatt acgcggtgat tcaacgcagc    1440
gcattcagcg tcgactgtgc aggtttttgcc cgcgggaaac ccgaattgc gcccacaacc    1500 tacacagtcg gcgtccctgg actggtgcgt ttcttggaag cacaccaccg agacccggac    1560
gcccaagcta tcgccgacga gctgaccgac gggcggttct actacgcgaa agtcgccagt    1620
gtcaccgacg ccggcgtgca gccggtgtat agccttcgtg tcgacacggc agaccacgcg    1680
tttatcacga acgggttcgt cagccacgct actggcctca ccggtctgaa ctcaggcctc    1740
acgacaaatc ctggtgtatc cgcttggcag gtcaacacag cttatactgc gggacaattg    1800
gtcacatata acggcaagac gtataaatgt ttgcagcccc acacctcctt ggcaggatgg    1860
```
gaaccatcca acgttcctgc cttgtggcag cttcaatga                               1899

<210> SEQ ID NO 20
<211> LENGTH: 7
<212> TYPE: PRT
<213> ORGANISM: Artificial Sequence
<220> FEATURE:
<223> OTHER INFORMATION: Gene sequence of designed peptide

<400> SEQUENCE: 20

Arg Arg Arg Arg Ser Gly Cys
1               5

<210> SEQ ID NO 21
<211> LENGTH: 7
<212> TYPE: PRT
<213> ORGANISM: Artificial Sequence
<220> FEATURE:
<223> OTHER INFORMATION: Designed peptide

<400> SEQUENCE: 21

Cys Gly Ser Glu Glu Glu Glu
1               5

<210> SEQ ID NO 22
<211> LENGTH: 342
<212> TYPE: PRT
<213> ORGANISM: JC-Polyomavirus

<400> SEQUENCE: 22

Met Gly Ala Ala Leu Ala Leu Leu Gly Asp Leu Val Ala Thr Val Ser
1               5                   10                  15

Glu Ala Ala Ala Ala Thr Gly Phe Ser Val Ala Glu Ile Ala Ala Gly
            20                  25                  30

Glu Ala Ala Ala Thr Ile Glu Val Glu Ile Ala Ser Leu Ala Thr Val
        35                  40                  45

Glu Gly Ile Thr Ser Thr Ser Glu Ala Ile Ala Ala Ile Gly Leu Thr
    50                  55                  60

Pro Glu Thr Tyr Ala Val Ile Thr Gly Ala Pro Gly Ala Val Ala Gly
65                  70                  75                  80

Phe Ala Ala Leu Val Gln Thr Val Thr Gly Gly Ser Ala Ile Ala Gln
            85                  90                  95

Leu Gly Tyr Arg Phe Phe Ala Asp Trp Asp His Lys Val Ser Thr Val
        100                 105                 110

Gly Leu Phe Gln Gln Pro Ala Met Ala Leu Gln Leu Phe Asn Pro Glu
    115                 120                 125

Asp Tyr Tyr Asp Ile Leu Phe Pro Gly Val Asn Ala Phe Val Asn Asn
130                 135                 140

Ile His Tyr Leu Asp Pro Arg His Trp Gly Pro Ser Leu Phe Ser Thr
145                 150                 155                 160

Ile Ser Gln Ala Phe Trp Asn Leu Val Arg Asp Asp Leu Pro Ala Leu
            165                 170                 175

Thr Ser Gln Glu Ile Gln Arg Arg Thr Gln Lys Leu Phe Val Glu Ser
        180                 185                 190

Leu Ala Arg Phe Leu Glu Glu Thr Thr Trp Ala Ile Val Asn Ser Pro
    195                 200                 205

Ala Asn Leu Tyr Asn Tyr Ile Ser Asp Tyr Tyr Ser Arg Leu Ser Pro
210                 215                 220

Val Arg Pro Ser Met Val Arg Gln Val Ala Gln Glu Gly Thr Tyr
225                 230                 235                 240

Ile Ser Phe Gly His Ser Tyr Thr Gln Ser Ile Asp Asp Ala Asp Ser
                245                 250                 255

Ile Gln Glu Val Thr Gln Arg Leu Asp Leu Lys Thr Pro Asn Val Gln
                260                 265                 270

Ser Gly Glu Phe Ile Glu Arg Ser Ile Ala Pro Gly Gly Ala Asn Gln
            275                 280                 285

Arg Ser Pro Gln Trp Met Leu Pro Leu Leu Leu Gly Leu Tyr Gly Thr
    290                 295                 300

Val Thr Pro Ala Leu Glu Ala Tyr Glu Asp Gly Pro Asn Lys Lys Lys
305                 310                 315                 320

Arg Arg Lys Glu Gly Pro Arg Ala Ser Lys Thr Ser Tyr Lys Arg Arg
                325                 330                 335

Ser Arg Ser Ser Arg Ser
            340

<210> SEQ ID NO 23
<211> LENGTH: 225
<212> TYPE: PRT
<213> ORGANISM: JC-Polyomavirus

<400> SEQUENCE: 23

Met Ala Leu Gln Leu Phe Asn Pro Glu Asp Tyr Tyr Asp Ile Leu Phe
1               5                   10                  15

Pro Gly Val Asn Ala Phe Val Asn Asn Ile His Tyr Leu Asp Pro Arg
            20                  25                  30

His Trp Gly Pro Ser Leu Phe Ser Thr Ile Ser Gln Ala Phe Trp Asn
        35                  40                  45

Leu Val Arg Asp Asp Leu Pro Ala Leu Thr Ser Gln Glu Ile Gln Arg
    50                  55                  60

Arg Thr Gln Lys Leu Phe Val Glu Ser Leu Ala Arg Phe Leu Glu Glu
65                  70                  75                  80

Thr Thr Trp Ala Ile Val Asn Ser Pro Ala Asn Leu Tyr Asn Tyr Ile
                85                  90                  95

Ser Asp Tyr Tyr Ser Arg Leu Ser Pro Val Arg Pro Ser Met Val Arg
                100                 105                 110

Gln Val Ala Gln Arg Glu Gly Thr Tyr Ile Ser Phe Gly His Ser Tyr
            115                 120                 125

Thr Gln Ser Ile Asp Asp Ala Asp Ser Ile Gln Glu Val Thr Gln Arg
130                 135                 140

Leu Asp Leu Lys Thr Pro Asn Val Gln Ser Gly Glu Phe Ile Glu Arg
145                 150                 155                 160

Ser Ile Ala Pro Gly Gly Ala Asn Gln Arg Ser Ala Pro Gln Trp Met
                165                 170                 175

Leu Pro Leu Leu Leu Gly Leu Tyr Gly Thr Val Thr Pro Ala Leu Glu
            180                 185                 190

Ala Tyr Glu Asp Gly Pro Asn Lys Lys Lys Arg Arg Lys Glu Gly Pro
        195                 200                 205

Arg Ala Ser Ser Lys Thr Ser Tyr Lys Arg Arg Ser Arg Ser Ser Arg
    210                 215                 220

Ser
225

<210> SEQ ID NO 24

```
<211> LENGTH: 36
<212> TYPE: PRT
<213> ORGANISM: JC-Polyomavirus

<400> SEQUENCE: 24

Ser Gly Glu Phe Ile Glu Arg Ser Ile Ala Pro Gly Gly Ala Asn Gln
1               5                   10                  15

Arg Ser Ala Pro Gln Trp Met Leu Pro Leu Leu Leu Gly Leu Tyr Gly
            20                  25                  30

Thr Val Thr Pro
        35

<210> SEQ ID NO 25
<211> LENGTH: 51
<212> TYPE: PRT
<213> ORGANISM: Homo sapiens (human)

<400> SEQUENCE: 25

Met Ala Arg Tyr Arg Cys Cys Arg Ser Gln Ser Arg Ser Arg Tyr Tyr
1               5                   10                  15

Arg Gln Arg Gln Arg Ser Arg Arg Arg Arg Arg Arg Ser Cys Gln Thr
            20                  25                  30

Arg Arg Arg Ala Met Arg Cys Cys Arg Pro Arg Tyr Arg Pro Arg Cys
        35                  40                  45

Arg Arg His
    50

<210> SEQ ID NO 26
<211> LENGTH: 21
<212> TYPE: PRT
<213> ORGANISM: Homo sapiens (human)

<400> SEQUENCE: 26

Ser Gln Ser Arg Ser Arg Tyr Tyr Arg Gln Arg Gln Arg Ser Arg Arg
1               5                   10                  15

Arg Arg Arg Arg Ser
            20

<210> SEQ ID NO 27
<211> LENGTH: 17
<212> TYPE: PRT
<213> ORGANISM: Human immunodeficiency virus (HIV)

<400> SEQUENCE: 27

Gly Arg Lys Lys Arg Arg Gln Arg Arg Arg Pro Pro Gln Lys Arg Lys
1               5                   10                  15

Gly

<210> SEQ ID NO 28
<211> LENGTH: 16
<212> TYPE: PRT
<213> ORGANISM: Drosophila spec.

<400> SEQUENCE: 28

Arg Gln Ile Lys Ile Trp Phe Gln Asn Arg Arg Met Lys Trp Lys Lys
1               5                   10                  15

<210> SEQ ID NO 29
<211> LENGTH: 21
<212> TYPE: PRT
<213> ORGANISM: Human papillomavirus type 33 (HPV33)
```

-continued

```
<400> SEQUENCE: 29

Phe Ile Leu Arg Arg Arg Lys Arg Phe Pro Tyr Phe Phe Thr Asp
1               5                   10                  15

Val Arg Val Ala Ala
            20

<210> SEQ ID NO 30
<211> LENGTH: 21
<212> TYPE: PRT
<213> ORGANISM: Human papillomavirus type 33 (HPV33)

<400> SEQUENCE: 30

Asp Asp Leu Arg Arg Arg Arg Lys Arg Phe Pro Tyr Phe Phe Thr Asp
1               5                   10                  15

Val Arg Val Ala Ala
            20

<210> SEQ ID NO 31
<211> LENGTH: 18
<212> TYPE: PRT
<213> ORGANISM: Artificial Sequence
<220> FEATURE:
<223> OTHER INFORMATION: Designed peptide

<400> SEQUENCE: 31

Arg Gly Gly Arg Leu Ser Tyr Ser Arg Arg Phe Ser Thr Ser Thr
1               5                   10                  15

Gly Arg

<210> SEQ ID NO 32
<211> LENGTH: 10
<212> TYPE: PRT
<213> ORGANISM: Artificial Sequence
<220> FEATURE:
<223> OTHER INFORMATION: Designed peptide

<400> SEQUENCE: 32

Arg Arg Leu Ser Tyr Ser Arg Arg Arg Phe
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Designed peptide

<400> SEQUENCE: 33

Pro Ile Arg Arg Arg Lys Lys Leu Arg Arg Leu Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Designed peptide

<400> SEQUENCE: 34

Arg Arg Gln Arg Arg Thr Ser Lys Leu Met Lys Arg
1               5                   10

<210> SEQ ID NO 35
<211> LENGTH: 15
```

```
<212> TYPE: PRT
<213> ORGANISM: Feline herpesvirus 1

<400> SEQUENCE: 35

Arg Arg Arg Arg Asn Arg Thr Arg Arg Asn Arg Arg Arg Val Arg
1               5                   10                  15

<210> SEQ ID NO 36
<211> LENGTH: 19
<212> TYPE: PRT
<213> ORGANISM: Brome mosaic virus

<400> SEQUENCE: 36

Lys Met Thr Arg Ala Gln Arg Arg Ala Ala Ala Arg Arg Asn Arg Trp
1               5                   10                  15

Thr Ala Arg

<210> SEQ ID NO 37
<211> LENGTH: 13
<212> TYPE: PRT
<213> ORGANISM: Human T-cell lymphotropic virus

<400> SEQUENCE: 37

Thr Arg Arg Gln Arg Thr Arg Arg Ala Arg Arg Asn Arg
1               5                   10

<210> SEQ ID NO 38
<211> LENGTH: 13
<212> TYPE: PRT
<213> ORGANISM: Human immunodeficiency virus (HIV)

<400> SEQUENCE: 38

Gly Arg Lys Lys Arg Arg Gln Arg Arg Arg Pro Pro Gln
1               5                   10

<210> SEQ ID NO 39
<211> LENGTH: 13
<212> TYPE: PRT
<213> ORGANISM: Human papillomavirus type 33 (HPV33)

<400> SEQUENCE: 39

Gly Arg Arg Arg Arg Arg Arg Arg Arg Arg Pro Pro Gln
1               5                   10

<210> SEQ ID NO 40
<211> LENGTH: 47
<212> TYPE: DNA
<213> ORGANISM: Artificial Sequence
<220> FEATURE:
<223> OTHER INFORMATION: Designed peptide

<400> SEQUENCE: 40
gaactagagg gtgcggatcc gaagaggaag agggttccca gcagtgg             47

<210> SEQ ID NO 41
<211> LENGTH: 45
<212> TYPE: DNA
<213> ORGANISM: Artificial Sequence
<220> FEATURE:
<223> OTHER INFORMATION: Gene sequence of designed peptide

<400> SEQUENCE: 41
gcttgttacc acaacctgat ctacgtctac ggttggtgaa catgc               45
```

<210> SEQ ID NO 42
<211> LENGTH: 7714
<212> TYPE: DNA
<213> ORGANISM: Artificial Sequence
<220> FEATURE:
<223> OTHER INFORMATION: Gene sequence of designed peptide

<400> SEQUENCE: 42

| | | | | | |
|---|---|---|---|---|---|
| aactacgtca | ggtggcactt | ttcggggaaa | tgtgcgcgga | acccctattt | gtttattttt | 60 |
| ctaaatacat | tcaaatatgt | atccgctcat | gagacaataa | ccctgataaa | tgcttcaata | 120 |
| atattgaaaa | aggaagagta | tgagtattca | acatttccgt | gtcgccctta | ttcccttttt | 180 |
| tgcggcattt | tgccttcctg | tttttgctca | cccagaaacg | ctggtgaaag | taaaagatgc | 240 |
| tgaagatcag | ttgggtgcac | gagtgggtta | catcgaactg | gatctcaaca | gcggtaagat | 300 |
| ccttgagagt | tttcgccccg | aagaacgttc | tccaatgatg | agcactttta | aagttctgct | 360 |
| atgtggcgcg | gtattatccc | gtgttgacgc | cgggcaagag | caactcggtc | gccgcataca | 420 |
| ctattctcag | aatgacttgg | ttgagtactc | accagtcaca | gaaaagcatc | ttacggatgg | 480 |
| catgacagta | agagaattat | gcagtgctgc | cataaccatg | agtgataaca | ctgcggccaa | 540 |
| cttacttctg | acaacgatcg | gaggaccgaa | ggagctaacc | gcttttttgc | acaacatggg | 600 |
| ggatcatgta | actcgccttg | atcgttggga | accggagctg | aatgaagcca | taccaaacga | 660 |
| cgagcgtgac | accacgatgc | ctgtagcaat | ggcaacaacg | ttgcgcaaac | tattaactgg | 720 |
| cgaactactt | actctagctt | cccggcaaca | attaatagac | tggatggagg | cggataaagt | 780 |
| tgcaggacca | cttctgcgct | cggcccttcc | ggctggctgg | tttattgctg | ataaatctgg | 840 |
| agccggtgag | cgtgggtctc | gcggtatcat | tgcagcactg | gggccagatg | gtaagccctc | 900 |
| ccgtatcgta | gttatctaca | cgacggggag | tcaggcaact | atggatgaac | gaaatagaca | 960 |
| gatcgctgag | ataggtgcct | cactgattaa | gcattggtaa | ctgtcagacc | aagtttactc | 1020 |
| atatatactt | tagattgatt | taccccggtt | gataatcaga | aaagccccaa | aacaggaag | 1080 |
| attgtataag | caaatattta | aattgtaaac | gttaatattt | tgttaaaatt | cgcgttaaat | 1140 |
| ttttgttaaa | tcagctcatt | ttttaaccaa | taggccgaaa | tcggcaaaat | cccttataaa | 1200 |
| tcaaaagaat | agcccgagat | agggttgagt | gttgttccag | tttggaacaa | gagtccacta | 1260 |
| ttaaagaacg | tggactccaa | cgtcaaaggg | cgaaaaaccg | tctatcaggg | cgatggccca | 1320 |
| ctacgtgaac | catcacccaa | atcaagtttt | ttggggtcga | ggtgccgtaa | agcactaaat | 1380 |
| cggaacccta | aagggagccc | ccgatttaga | gcttgacggg | gaaagccggc | gaacgtggcg | 1440 |
| agaaaggaag | ggaagaaagc | gaaaggagcg | ggcgctaggg | cgctggcaag | tgtagcggtc | 1500 |
| acgctgcgcg | taaccaccac | acccgccgcg | cttaatgcgc | cgctacaggg | cgcgtaaaag | 1560 |
| gatctaggtg | aagatccttt | ttgataatct | catgaccaaa | atcccttaac | gtgagttttc | 1620 |
| gttccactga | gcgtcagacc | ccgtagaaaa | gatcaaagga | tcttcttgag | atcctttttt | 1680 |
| tctgcgcgta | atctgctgct | tgcaaacaaa | aaaaccaccg | ctaccagcgg | tggtttgttt | 1740 |
| gccggatcaa | gagctaccaa | ctctttttcc | gaaggtaact | ggcttcagca | gagcgcagat | 1800 |
| accaaatact | gtccttctag | tgtagccgta | gttaggccac | cacttcaaga | actctgtagc | 1860 |
| accgcctaca | tacctcgctc | tgctaatcct | gttaccagtg | gctgctgcca | gtggcgataa | 1920 |
| gtcgtgtctt | accgggttgg | actcaagacg | atagttaccg | gataaggcgc | agcggtcggg | 1980 |
| ctgaacgggg | ggttcgtgca | cacagcccag | cttggagcga | acgacctaca | ccgaactgag | 2040 |
| atacctacag | cgtgagctat | gagaaagcgc | cacgcttccc | gaagggagaa | aggcggacag | 2100 |

```
gtatccggta agcggcaggg tcggaacagg agagcgcacg agggagcttc caggggaaa    2160 cgcctggtat ctttatagtc ctgtcgggtt tcgccacctc tgacttgagc gtcgatttt     2220 gtgatgctcg tcagggggc ggagcctatg aaaaacgcc agcaacgcgg ccttttacg       2280 gttcctggcc ttttgctggc cttttgctca catgttcttt cctgcgttat ccctgattc     2340 tgtggataac cgtattaccg cctttgagtg agctgatacc gctcgccgca gccgaacgac   2400
cgagcgcagc gagtcagtga gcgaggaagc tatggtgcac tctcagtaca atctgctctg   2460
atgccgcata gttaagccag tatacactcc gctatcgcta cgtgactggg tcatggctgc   2520
gccccgacac ccgccaacac ccgctgacgc gccctgacgg gcttgtctgc tcccggcatc   2580
cgcttacaga caagctgtga ccgtctccgg gagctgcatg tgtcagaggt tttcaccgtc   2640
atcaccgaaa cgcgcgaggc agctgcggta aagctcatca gcgtggtcgt gcagcgattc   2700
acagatgtct gcctgttcat ccgcgtccag ctcgttgagt ttctccagaa gcgttaatgt   2760
ctggcttctg ataaagcggg ccatgttaag ggcggttttt tcctgtttgg tcactgatgc   2820
ctccgtgtaa gggggatttc tgttcatggg ggtaatgata ccgatgaaac gagagaggat   2880
gctcacgata cgggttactg atgatgaaca tgcccggtta ctggaacgtt gtgagggtaa   2940
acaactggcg gtatgatgc ggcgggacca gagaaaaatc actcagggtc aatgccagcc    3000
gaacgccagc aagacgtagc ccagcgcgtc ggccgccatg ccggcgataa tggcctgctt   3060
ctcgccgaaa cgtttggtgg cgggaccagt gacgaaggct tgagcgaggg cgtgcaagat   3120
tccgaatacc gcaagcgaca ggccgatcat cgtcgcgctc cagcgaaagc ggtcctcgcc   3180
gaaaatgacc cagagcgctg ccggcacctg tcctacgagt tgcatgataa agaagacagt   3240
cataagtgcg gcgacgatag tcatgccccg cgcccaccgg aaggagctga ctgggttgaa   3300
ggctctcaag ggcatcggtc gagatcccgg tgcctaatga gtgagctaac ttacattaat   3360
tgcgttgcgc tcactgcccg ctttccagtc gggaaacctg tcgtgccagc tgcattaatg   3420
aatcggccaa cgcgcgggga gaggcggttt gcgtattggg cgccagggtg ttttttcttt    3480
tcaccagtga cgggcaac agctgattgc ccttcaccgc ctggccctga gagagttgca     3540
gcaagcggtc cacgctggtt tgccccagca ggcgaaaatc ctgtttgatg gtggttaacg   3600
gcgggatata acatgagctg tcttcggtat cgtcgtatcc cactaccgag atatccgcac   3660
caacgcgcag cccggactcg gtaatggcgc gcattgcgcc cagcgccatc tgatcgttgg   3720
caaccagcat cgcagtggga acgatgccct cattcagcat ttgcatggtt tgttgaaaac   3780
cggacatggc actccagtcg ccttcccgtt ccgctatcgg ctgaatttga ttgcgagtga   3840
gatatttatg ccagccagcc agacgcagac gcgccgagac agaacttaat gggcccgcta   3900
acagcgcgat ttgctggtga cccaatgcga ccagatgctc cacgcccagt cgcgtaccgt   3960
cttcatggga gaaaataata ctgttgatgg gtgtctggtc agagacatca agaaataacg   4020
ccggaacatt agtgcaggca gcttccacag caatggcatc ctggtcatcc agcggatagt   4080
taatgatcag cccactgacg cgttgcgcga agattgtg caccgccgct ttacaggctt     4140
cgacgccgct tcgttctacc atcgacacca ccacgctggc acccagttga tcggcgcgag   4200
atttaatcgc cgcgacaatt tgcgacgcg cgtgcagggc cagactggag gtggcaacgc    4260
caatcagcaa cgactgtttg cccgccagtt gttgtgccac gcggttggga atgtaattca   4320
gctccgccat cgccgcttcc acttttcc gcgttttcgc agaaacgtgg ctggcctggt     4380
tcaccacgcg ggaacggtc tgataagaga caccggcata ctctgcgaca tcgtataacg    4440
ttactggttt cacattcacc accctgaatt gactctcttc cgggcgctat catgccatac   4500
```

-continued

```
cgcgaaaggt tttgcgccat tcgatggtgt ccgggatctc gacgctctcc cttatgcgac    4560
tcctgcatta ggaagcagcc cagtagtagg ttgaggccgt tgagcaccgc cgccgcaagg    4620
aatggtgcat gccggcatgc cgcccttttcg tcttcaagaa ttaattccca attccccagg   4680
catcaaataa aacgaaaggc tcagtcgaaa gactgggcct ttcgttttat ctgttgtttg    4740
tcggtgaacg ctctcctgag taggacaaat ccgccgggag cggatttgaa cgttgcgaag    4800
caacggcccg gagggtggcg ggcaggacgc ccgccataaa ctgccaggaa ttaattcccc    4860
aggcatcaaa taaaacgaaa ggctcagtcg aaagactggg cctttcgttt tatctgttgt    4920
ttgtcggtga acgctctcct gagtaggaca atccgccgg gagcggattt gaacgttgcg     4980
aagcaacggc ccggagggtg gcgggcagga cgcccgccat aaactgccag gaattaattc    5040
cccaggcatc aaataaaacg aaaggctcag tcgaaagact gggccttttcg ttttatctgt   5100 tgtttgtcgg tgaacgctct cctgagtagg acaaatccgc cgggagcgga tttgaacgtt    5160
gcgaagcaac ggcccggagg gtggcgggca ggacgcccgc cataaactgc caggaattaa    5220
ttccccaggc atcaaataaa acgaaaggct cagtcgaaag actgggcctt tcgttttatc    5280
tgttgtttgt cggtgaacgc tctcctgagt aggacaaatc cgccgggagc ggatttgaac    5340
gttgcgaagc aacggcccgg agggtggcgg gcaggacgcc cgccataaac tgccaggaat    5400
taattcccca ggcatcaaat aaaacgaaag gctcagtcga aagactgggc ctttcgtttt    5460
atctgttgtt tgtcggtgaa cgctctcctg agtaggacaa atccgccggg agcggatttg    5520
aacgttgcga agcaacggcc cggagggtgg cgggcaggac gcccgccata aactgccagg    5580
aattggggat cggaattaat tccggtttta accgggat ctcgatcccg cgaaattaat      5640
acgactcact ataggggaat gtgagcgga taacaattcc cctctagaaa taattttgtt     5700
taactttaag aaggagatat acatatggct cccaccaagc gcaagggcga gcccaaggac    5760
cccgtgcaag tgcccaagct gctgatccgt ggtggtgtcg aggtgctgga agtcaagacc    5820
ggcgtggact ccattaccga ggtggagtgc ttcctcaccc ccgagatggg tgaccctgac    5880
gagcacctga ggggcttctc caagtccatc tccatctccg acccttcga gtccgactcc    5940 cccaaccgtg acatgctgcc ctgctactcc gtggctcgta tcccctgcc caacctgaac    6000 gaggacctga cttgcggcaa catcctgatg tgggaggctg tgaccctcaa gaccgaggtc    6060
atcggcgtga cttccctgat gaacgtgcac tccaacggcc aggctaccca cgacaacggt    6120
gctggcaagc ccgtgcaggg aacctccttc cacttcttct ccgtgggtgg cgaggctctg    6180
gaactccagg gcgtggtgtt caactaccgt accaagtacc ccgacggcac catcttcccc    6240
aagaacgcta ctgtgcagtc ccaagtgatg aacaccgagc acaaggctta cctggacaag    6300
aacaaggcct accccgtgga gtgctgggtg cccgacccca ccgtaacga gaacacccgt    6360 tacttcggca ccctgaccgg tggagagaac gtgcccccccg tgctgcacat caccaacacc    6420
gctaccaccg tgctgctgga cgagttcggt gtcggtcccc tgtgcaaggg cgacaacctg    6480
tacctgtccg ctgtggacgt gtgcggcatg ttcaccaacc gttccggttc ccagcagtgg    6540
cgtggcctgt cccgctactt caaggtgcag ctgcgcaagc gtcgtgtgaa gaaccccctac    6600 cctatctcct tcctgctgac cgacctgatc aaccgtcgta ccccctcgtgt ggacggccag    6660 cccatgtacg gcatggacgc tcaggtggaa gaggtccgcg tgttcgaggg caccgaggaa    6720
ttgcccggcg acccccgacat gatgcgttac gtggacaagt acggccagct ccagaccaag    6780
atgtgcatca cgggagatgc actagttgcc ctacccgagg gcgagtcggt acgcatcgcc    6840
```

-continued

```
gacatcgtgc cgggtgcgcg gcccaacagt gacaacgcca tcgacctgaa agtccttgac    6900
cggcatggca atcccgtgct cgccgaccgg ctgttccact ccggcgagca tccggtgtac    6960
acggtgcgta cggtcgaagg tctgcgtgtg acgggcaccg cgaaccaccc gttgttgtgt    7020
ttggtcgacg tcgccggggt gccgacccctg ctgtggaagc tgatcgacga aatcaagccg    7080
ggcgattacg cggtgattca acgcagcgca ttcagcgtcg actgtgcagg ttttgcccgc    7140
gggaaacccg aatttgcgcc cacaacctac acagtcggcg tccctggact ggtgcgtttc    7200
ttggaagcac accaccgaga cccggacgcc caagctatcg ccgacgagct gaccgacggg    7260
cggttctact acgcgaaagt cgccagtgtc accgacgccg gcgtgcagcc ggtgtatagc    7320
cttcgtgtcg acacggcaga ccacgcgttt atcacgaacg ggttcgtcag ccacgctact    7380
ggcctcaccg gtctgaactc aggcctcacg acaaatcctg gtgtatccgc ttggcaggtc    7440
aacacagctt atactgcggg acaattggtc acatataacg gcaagacgta taaatgtttg    7500
cagccccaca cctccttggc aggatgggaa ccatccaacg ttcctgcctt gtggcagctt    7560
caatgactgc aggaagggga tccggctgct aacaaagccc gaaaggaagc tgagttggct    7620
gctgccaccg ctgagcaata actagcataa ccccttgggg cctctaaacg gtcttgagg    7680 ggttttttgc tgaaaggagg aactatatcc ggat                              7714
```

<210> SEQ ID NO 43
<211> LENGTH: 45
<212> TYPE: DNA
<213> ORGANISM: Artificial Sequence
<220> FEATURE:
<223> OTHER INFORMATION: Gene sequence of designed peptide

<400> SEQUENCE: 43
gaactagagg gtgcggatcc gaagaggaag agggtgctgg caagc    45

<210> SEQ ID NO 44
<211> LENGTH: 45
<212> TYPE: DNA
<213> ORGANISM: Artificial Sequence
<220> FEATURE:
<223> OTHER INFORMATION: Gene sequence of designed peptide

<400> SEQUENCE: 44
gcttgttacc acaacctgat ctacgtctac ggtgggtagc ctggc    45

<210> SEQ ID NO 45
<211> LENGTH: 4
<212> TYPE: PRT
<213> ORGANISM: Artificial Sequence
<220> FEATURE:
<223> OTHER INFORMATION: Designed interaction region peptide

<400> SEQUENCE: 45

Glu Glu Arg Arg
1

<210> SEQ ID NO 46
<211> LENGTH: 4
<212> TYPE: PRT
<213> ORGANISM: Artificial Sequence
<220> FEATURE:
<223> OTHER INFORMATION: Designed interaction region peptide

<400> SEQUENCE: 46

Glu Arg Glu Arg
1

```
<210> SEQ ID NO 47
<211> LENGTH: 6
<212> TYPE: PRT
<213> ORGANISM: Artificial Sequence
<220> FEATURE:
<223> OTHER INFORMATION: Designed interaction region peptide

<400> SEQUENCE: 47

Glu Glu Arg Arg Glu Glu
1               5

<210> SEQ ID NO 48
<211> LENGTH: 6
<212> TYPE: PRT
<213> ORGANISM: Artificial Sequence
<220> FEATURE:
<223> OTHER INFORMATION: Designed interaction region peptide

<400> SEQUENCE: 48

Arg Arg Glu Glu Arg Arg
1               5

<210> SEQ ID NO 49
<211> LENGTH: 6
<212> TYPE: PRT
<213> ORGANISM: Artificial Sequence
<220> FEATURE:
<223> OTHER INFORMATION: Designed interaction region peptide

<400> SEQUENCE: 49

Glu Glu Glu Arg Arg Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Designed interaction region peptide

<400> SEQUENCE: 50

Asp Asp Glu Arg Lys Lys
1               5

<210> SEQ ID NO 51
<211> LENGTH: 5
<212> TYPE: PRT
<213> ORGANISM: Artificial Sequence
<220> FEATURE:
<223> OTHER INFORMATION: Designed interaction region peptide

<400> SEQUENCE: 51

Asp Asp Asp Arg Arg
1               5

<210> SEQ ID NO 52
<211> LENGTH: 5
<212> TYPE: PRT
<213> ORGANISM: Artificial Sequence
<220> FEATURE:
<223> OTHER INFORMATION: Designed interaction region peptide

<400> SEQUENCE: 52

Arg Arg Arg Arg Glu
1               5
```

```
<210> SEQ ID NO 53
<211> LENGTH: 5
<212> TYPE: PRT
<213> ORGANISM: Artificial Sequence
<220> FEATURE:
<223> OTHER INFORMATION: Designed interaction region peptide

<400> SEQUENCE: 53

Glu Glu Glu Glu Arg
1               5

<210> SEQ ID NO 54
<211> LENGTH: 4
<212> TYPE: PRT
<213> ORGANISM: Artificial Sequence
<220> FEATURE:
<223> OTHER INFORMATION: Designed interaction region peptide

<400> SEQUENCE: 54

Glu Glu Glu Glu
1

<210> SEQ ID NO 55
<211> LENGTH: 4
<212> TYPE: PRT
<213> ORGANISM: Artificial Sequence
<220> FEATURE:
<223> OTHER INFORMATION: Designed interaction region peptide

<400> SEQUENCE: 55

Arg Arg Arg Arg
1

<210> SEQ ID NO 56
<211> LENGTH: 7
<212> TYPE: PRT
<213> ORGANISM: Artificial Sequence
<220> FEATURE:
<223> OTHER INFORMATION: Designed interaction region peptide

<400> SEQUENCE: 56

Glu Gly Glu Gly Glu Gly Glu
1               5

<210> SEQ ID NO 57
<211> LENGTH: 7
<212> TYPE: PRT
<213> ORGANISM: Artificial Sequence
<220> FEATURE:
<223> OTHER INFORMATION: Designed interaction region peptide

<400> SEQUENCE: 57

Arg Gly Arg Gly Arg Gly Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Designed interaction region peptide

<400> SEQUENCE: 58

Glu Ser Glu Ser Glu Ser Glu
1               5
```

```
<210> SEQ ID NO 59
<211> LENGTH: 7
<212> TYPE: PRT
<213> ORGANISM: Artificial Sequence
<220> FEATURE:
<223> OTHER INFORMATION: Designed interaction region peptide

<400> SEQUENCE: 59

Arg Ser Arg Ser Arg Ser Arg
1               5

<210> SEQ ID NO 60
<211> LENGTH: 3
<212> TYPE: PRT
<213> ORGANISM: Artificial Sequence
<220> FEATURE:
<223> OTHER INFORMATION: Designed peptide

<400> SEQUENCE: 60

Arg Gly Asp
1

<210> SEQ ID NO 61
<211> LENGTH: 19
<212> TYPE: PRT
<213> ORGANISM: Artificial Sequence
<220> FEATURE:
<223> OTHER INFORMATION: Designed peptide

<400> SEQUENCE: 61

Cys Lys Asn Glu Lys Lys Asn Lys Ile Glu Arg Asn Asn Lys Leu Lys
1               5                   10                  15

Gln Pro Pro

<210> SEQ ID NO 62
<211> LENGTH: 5
<212> TYPE: PRT
<213> ORGANISM: Artificial Sequence
<220> FEATURE:
<223> OTHER INFORMATION: Designed peptide

<400> SEQUENCE: 62

Cys Gly Lys Arg Lys
1               5

<210> SEQ ID NO 63
<211> LENGTH: 9
<212> TYPE: PRT
<213> ORGANISM: Artificial Sequence
<220> FEATURE:
<223> OTHER INFORMATION: Designed peptide

<400> SEQUENCE: 63

Cys Ser Arg Pro Arg Arg Ser Glu Cys
1               5

<210> SEQ ID NO 64
<211> LENGTH: 9
<212> TYPE: PRT
<213> ORGANISM: Artificial Sequence
<220> FEATURE:
<223> OTHER INFORMATION: Designed peptide

<400> SEQUENCE: 64

Cys Arg Glu Ala Gly Arg Lys Ala Cys
1               5
```

```
<210> SEQ ID NO 65
<211> LENGTH: 9
<212> TYPE: PRT
<213> ORGANISM: Artificial Sequence
<220> FEATURE:
<223> OTHER INFORMATION: Designed peptide

<400> SEQUENCE: 65

Cys Ala Gly Arg Arg Ser Ala Tyr Cys
1               5

<210> SEQ ID NO 66
<211> LENGTH: 12
<212> TYPE: PRT
<213> ORGANISM: Artificial Sequence
<220> FEATURE:
<223> OTHER INFORMATION: Designed peptide

<400> SEQUENCE: 66

Cys Met Gly Thr Ile Asn Thr Arg Thr Lys Lys Cys
1               5                   10

<210> SEQ ID NO 67
<211> LENGTH: 6
<212> TYPE: PRT
<213> ORGANISM: Artificial Sequence
<220> FEATURE:
<223> OTHER INFORMATION: Designed peptide

<400> SEQUENCE: 67

Cys Lys Ala Ala Lys Asn
1               5

<210> SEQ ID NO 68
<211> LENGTH: 9
<212> TYPE: PRT
<213> ORGANISM: Artificial Sequence
<220> FEATURE:
<223> OTHER INFORMATION: Designed peptide

<400> SEQUENCE: 68

Cys Ser Asn Arg Asp Ala Arg Arg Cys
1               5

<210> SEQ ID NO 69
<211> LENGTH: 9
<212> TYPE: PRT
<213> ORGANISM: Artificial Sequence
<220> FEATURE:
<223> OTHER INFORMATION: Designed peptide

<400> SEQUENCE: 69

Cys Gly Asn Ser Asn Pro Lys Ser Cys
1               5

<210> SEQ ID NO 70
<211> LENGTH: 9
<212> TYPE: PRT
<213> ORGANISM: Artificial Sequence
<220> FEATURE:
<223> OTHER INFORMATION: Designed peptide

<400> SEQUENCE: 70

Cys Ser Arg Glu Ser Pro His Pro Cys
1               5
```

```
<210> SEQ ID NO 71
<211> LENGTH: 12
<212> TYPE: PRT
<213> ORGANISM: Artificial Sequence
<220> FEATURE:
<223> OTHER INFORMATION: Designed peptide

<400> SEQUENCE: 71

Ala Ser Gly Ala Leu Ser Pro Ser Arg Leu Asp Thr
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Designed peptide

<400> SEQUENCE: 72

Cys Arg Lys Arg Leu Asp Arg Asn Cys
1               5

<210> SEQ ID NO 73
<211> LENGTH: 9
<212> TYPE: PRT
<213> ORGANISM: Artificial Sequence
<220> FEATURE:
<223> OTHER INFORMATION: Designed peptide

<400> SEQUENCE: 73

Cys Leu Ser Tyr Tyr Pro Ser Tyr Cys
1               5

<210> SEQ ID NO 74
<211> LENGTH: 7
<212> TYPE: PRT
<213> ORGANISM: Artificial Sequence
<220> FEATURE:
<223> OTHER INFORMATION: Designed peptide

<400> SEQUENCE: 74

Arg Arg Arg Arg Ser Gly Cys
1               5

<210> SEQ ID NO 75
<211> LENGTH: 7
<212> TYPE: PRT
<213> ORGANISM: Artificial Sequence
<220> FEATURE:
<223> OTHER INFORMATION: Designed peptide

<400> SEQUENCE: 75

Cys Ser Gly Glu Glu Glu Glu
1               5

<210> SEQ ID NO 76
<211> LENGTH: 5
<212> TYPE: PRT
<213> ORGANISM: Artificial Sequence
<220> FEATURE:
<223> OTHER INFORMATION: Designed peptide

<400> SEQUENCE: 76

Arg Arg Arg Arg Cys
1               5

<210> SEQ ID NO 77
```

```
<211> LENGTH: 5
<212> TYPE: PRT
<213> ORGANISM: Artificial Sequence
<220> FEATURE:
<223> OTHER INFORMATION: Designed peptide

<400> SEQUENCE: 77

Cys Glu Glu Glu Glu
1               5

<210> SEQ ID NO 78
<211> LENGTH: 23
<212> TYPE: DNA
<213> ORGANISM: Artificial Sequence
<220> FEATURE:
<223> OTHER INFORMATION: Gene sequence of designe peptide

<400> SEQUENCE: 78
gattcatgcg gatccgaaga gga                                              23

<210> SEQ ID NO 79
<211> LENGTH: 29
<212> TYPE: DNA
<213> ORGANISM: Artificial Sequence
<220> FEATURE:
<223> OTHER INFORMATION: Gene sequence of designed peptide

<400> SEQUENCE: 79
acctctacca caacctgatc tacgtctac                                        29
```

JC POLYOMAVIRUS VLP (VIRUS-LIKE PARTICLE) WITH A TARGETING PEPTIDE

FIELD OF THE INVENTION

The present invention relates to a fusion protein comprising a peptide with a targeting region and a first and a second interaction region for targeting the fusion protein and to virus like particles (VLP) comprising the fusion protein for use as drug delivery system.

BACKGROUND OF THE INVENTION

In the development of specific diagnostic or therapeutic procedures, the use of transfer systems (delivery systems) that allow a possible cell-specific transfer of substances and nucleic acids such as, markers or agents, is of great importance. For this cell-specific transfer systems based on virus-like particles (VLP) have been developed. One of these systems is the VLP from the human polyomavirus John-Cunningham virus (JCV) as described in WO 97/19174 and EP 1270586 B1. Basis of this system is the ability of the VLP to package foreign cargo such as drugs or and nucleic acids instead of the viral DNA. As a VLP still has the ability to specifically recognize cells and to be internalized by the cells the VLP can be used to introduce a cargo of choice into specific cells. However, the VLPs of the state art interact with a very broad spectrum of cells. For certain applications it is desirable to be able to address only specific cell types.

In view of this prior art it is an object of the present invention to improve VLPs for the use as a drug delivery system. In particular it is an object of the present invention to provide means to improve the cell specificity of VLPs.

SUMMARY OF THE INVENTION

According to a first aspect, the invention provides a fusion protein comprising at least a first and a second peptide, wherein

- the second peptide comprises a targeting region and a first and a second interaction region,
- the second peptide is located on the surface of the fusion protein,
- the second peptide comprises at least two interaction pairs, wherein an interaction pair is formed by an amino acid of the first interaction region and an amino acid of the second interaction region,
- the interaction region between the amino acid of an interaction pair is covalent or non-covalent, and
- at least one interaction pair is a covalent interaction pair in which the amino acids are covalently bound.

The second peptide according to the invention is a modular targeting peptide that has several advantages for targeting a protein of interest to which it is fused forming the fusion protein. The second peptide provides a self-forming secondary structure that presents a specific targeting sequence of choice in form of a loop spaced apart from the surface of the fusion protein. Due to the spacing of the targeting sequence away from the surface of the fusion protein, the second peptide provides an improved accessibility of the targeting sequence. The fusion protein may be used in particular in combination with a virus-like particle (VLP) cargo transport to provide to the VLP the ability to target specific predefined receptors/cell types.

Thus, according to the second aspect, the invention provides a VLP comprising the fusion peptide of the first aspect of the invention.

According to a third aspect, the invention provides a pharmaceutical composition comprising the VLP according to the second aspect and at least one pharmaceutically acceptable carrier.

According to a fourth aspect, the invention provides an isolated polynucleotide comprising a nucleic acid sequence encoding a fusion protein according to the first aspect of the invention. According to a fifth aspect, the invention provides an expression vector comprising the nucleotide according to the fourth aspect of the invention.

According to a sixth aspect, the invention provides a host cell comprising the expression vector according to the fifth aspect of the invention.

According to a seventh aspect, the invention provides a process of producing the VLP according to the second aspect of the invention which comprises the steps of:

a) introducing a polynucleotide according to the second aspect of the invention into a host cell;
b) culturing the transformed host cell in a medium under conditions leading to a protein expression with the polynucleotide as a template,
c) isolating the expression product from the cell and
d) assembly of the expression product optionally with further viral proteins into the VLP

BRIEF DESCRIPTION OF THE FIGURES

FIG. 1 shows two specific embodiments of the second peptide according to the invention (a and b)

FIG. 2 provides an overview of a specific embodiment for the production of VLPs comprising a fusion protein according to the invention.

FIG. 3 shows histograms calculated from flow cytometry data obtained from MDA-MB-231 cells treated with VLPs. The histograms a) to c) correspond to the following VLPs:

a) VLP with VP1 and VP1-FITC, VLP with VP1-DE-Loop-Lyp1 and VP1-FITC, VLP with VP1-HI-Loop-Lyp1 and VP1-FITC
b) VLP with VP1 and VP1-Dylight488, VLP with VP1-DE-Loop-Lyp1 and VP1-Dylight488, VLP with VP1-HI-Loop-Lyp1 and VP1-Dylight488
c) VLP with VP1 and VP1-Atto647, VLP with VP1-DE-Loop-Lyp1 and VP1-Atto647, VLP with VP1-HI-Loop-Lyp1 and VP1-Atto647.

The X-axis represents the measured intensity of the signal, the Y-axis the number of cells with the specific signal intensity.

FIG. 4 shows a column diagram representation of the flow cytometry data obtained from MDA-MB-231 cells treated with VLPs. Each column represents the percentage of cells—identified by a minimum signal strength—with a positive uptake of a specific type combination of VLP and fluorescent dye as indicated below the columns. Three different VLPs are tested: VLPs containing VP1-DE-Loop-Lyp1 or VP1-HI-Loop-Lyp1 VLPs from normal VP1. Also three different dyes are tested: FITC, Atto-488 and Atto 647.

FIG. 5 shows the detection of VLP in spheroids of a breast cancer spheroid model. The following VLPs were tested: VP1, VP1-HI-Loop-linRGD, and VP1-HI-Loop-cycRGD, each labelled with Atto-488. A mock probe was used as a control.

FIG. 6 study design of an orthotopic breast cancer tumor model

FIG. 7 shows the flow cytometry analysis of the tumor cells from the orthotopic breast cancer tumor model of FIG.

6. Nine animals had been treated with a VLP comprising VP1-HI-Loop-Lyp1 and three animals were used as control.

DETAILED DESCRIPTION OF THE INVENTION

1. Definitions

A "peptide" according to the present invention may be composed of any number of amino acids of any type, preferably naturally occurring amino acids, which preferably are linked by peptide bonds. In particular, a peptide comprises at least 3 amino acids, preferably at least 5, at least 7, at least 9, at least 12 or at least 15 amino acids. Furthermore, there is no upper limit for the length of a peptide. However, preferably a peptide according to the invention does not exceed a length of 500 amino acids, more preferably, it does not exceed a length of 300 amino acids; even more preferably, it is not longer than 250 amino acids. Thus, the term peptide includes oligopeptides, which usually refer to peptides with a length of 2 to 10 amino acids, and polypeptides, which usually refer to peptides with a length of more than 10 amino acids. The term "protein" refers to a peptide with at least 60, at least 80, preferably at least 100 amino acids.

The term "fusion protein" according to the invention relates to proteins or peptides created through the joining of two or more genes that originally coded for separate proteins. The genes may be naturally occurring from the same organism or different organisms or may be synthetic polynucleotides.

The term "exogenous" according to the invention relates to the property of a peptide or polynucleotide that it does not naturally occur in polyomaviruses.

The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Desoxyribonucleotides×100)/(Length of Alignment–Total Number of Gaps in Alignment)

The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature.

The term "operably linked" means a configuration in which a control sequence is placed at an appropriate position relative to the coding sequence of a polynucleotide such that the control sequence directs the expression of the coding sequence. Expression: The term "expression" includes any step involved in the production of the polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to additional nucleotides that provide for its expression.

The term "host cell" means any cell type that is susceptible to transformation, transfection, transduction, and the like, with a nucleic acid construct or expression vector comprising a polynucleotide of the present invention. The term "host cell" encompasses any progeny of a parent cell that is not identical to the parent cell due to mutations that occur during replication.

The term "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The term "carrier" applied to pharmaceutical compositions of the invention refers to a diluent, excipient, or vehicle with which the VLP of the invention is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington The Science and Practice of Pharmacy," 21th edition, (David B. Troy ed., 2006, p. 745-775, p. 802-836 and p. 837-849).

As used herein, the term "pharmaceutical composition" refers to any composition comprising at least the VLP with or without cargo and at least one other ingredient, as well as any product which results, directly or indirectly, from combination, complexation, or aggregation of any two or more of the ingredients, from dissociation of one or more of the ingredients, or from other types of reactions or interactions of one or more of the ingredients. Accordingly, the term "pharmaceutical composition" as used herein may encompass, inter alia, any composition made by admixing a pharmaceutically active ingredient and one or more pharmaceutically acceptable carriers.

The term "low stringency conditions" means for probes of at least 100 nucleotides in length, prehybridization and hybridization at 42 degrees centigrade in 5×SSPE, 0.3 percent SDS, 200 micrograms/ml sheared and denatured salmon sperm DNA, and 25 percent formamide, following standard Southern blotting procedures for 12 to 24 hours. The carrier material is finally washed three times each for 15 minutes using 2×SSC, 0.2 percent SDS at 50 degrees centigrade.

The term "medium stringency conditions" means for probes of at least 100 nucleotides in length, prehybridization and hybridization at 42 degrees centigrade in 5×SSPE, 0.3 percent SDS, 200 micrograms/ml sheared and denatured salmon sperm DNA, and 35 percent formamide, following standard Southern blotting procedures for 12 to 24 hours. The carrier material is finally washed three times each for 15 minutes using 2×SSC, 0.2% SDS at 55° C.

The term "high stringency conditions" means for probes of at least 100 nucleotides in length, prehybridization and hybridization at 42 degrees centigrade in 5×SSPE, 0.3 percent SDS, 200 micrograms/ml sheared and denatured salmon sperm DNA, and 50 percent formamide, following standard Southern blotting procedures for 12 to 24 hours. The carrier material is finally washed three times each for 15 minutes using 2×SSC, 0.2% SDS at 65° C.

The term "PBS" means phosphate buffered saline. It is a water-based salt solution containing sodium phosphate, sodium chloride and, in some formulations, potassium chloride and potassium phosphate. The osmolarity and ion concentrations of the solutions match those of the human body.

2. Fusion Protein

According to a first aspect, the invention provides a fusion protein comprising at least a first and a second peptide, wherein:
 the second peptide comprises a targeting region and a first and a second interaction region,
 the second peptide is located on the surface of the fusion protein,
 the second peptide comprises at least two interaction pairs, wherein an interaction pair is formed by an amino acid of the first interaction region and an amino acid of the second interaction region,
 the interaction region between the amino acid of an interaction pair is covalent or non-covalent, and
 at least one interaction pair is a covalent interaction pair in which the amino acids are covalently bound.

The second peptide according to the invention, i.e. the targeting peptide, is based on a particular secondary structure resembling a hair pin known from single-stranded polynucleotides especially in RNA molecules. When folded into its secondary structure, the peptide preferably comprises two paired regions of the amino acid sequence, the first and second interaction region and an unpaired loop comprising the targeting region as shown schematically in FIGS. 1a and b.

The targeting region according to the invention comprises an amino acid sequence—the targeting sequence—that is known to interact with a target of interest, in particular a cellular receptor. The secondary structure of the second peptide may also be described as a stem loop comprising a stem region and a loop region. Accordingly, the two interaction regions of the peptide preferably form the stem and the targeting region forms the loop (see FIGS. 1a and b). When located on the surface of the fusion protein, the stem, i.e. the first and second interaction region of the second peptide, lead to a sufficient spacing between the surface of the protein and the targeting region so that an interaction with a targeting recognizing means, in particular a cellular receptor, is possible without steric hindrance.

The folding of the structure is based on the following theoretic principle. During protein folding, the amino acids on the first and second interaction region get into proximity. When two complementary amino acids of the two interaction regions get in proximity to each other, they will transiently bind to each other, i.e. interact non-covalently, and, thus, form a non-covalent interaction pair. The more interaction pairs are formed at a time, the higher is the binding strength and the longer the transient interaction of the two interaction regions. The interaction pairs of the second peptide are preferably set up such that the formation of these non-covalent interaction pairs brings the amino acids of the covalent interaction pair, in particular cysteines, into proximity to each other for a sufficient time so as to allow formation of a covalent bond, e.g. a disulfide-bridge. The formation of the covalent interaction pair leads to a further stabilization of the interaction of the first and second interaction region of the second peptide. Accordingly, the final secondary structure of the second peptide with a loop including the targeting region and a stem formed by the first and second interaction region is formed. The loop can be regarded as a circular peptide connected by a covalent interaction pair. It was shown for a variety of signaling/targeting peptides that a circular shape of the peptide improves its recognition by the specific receptor.

Thus, according to one embodiment of the first aspect of the invention, the amino acid sequence of the targeting region is located between the amino acid sequences of the first and second interaction region. A location of the amino acid sequence of the targeting region between the first and second interaction region is required to obtain a targeting region that is located in the loop of the folded second peptide.

The amino acid sequence of the targeting region may overlap with the amino acid sequences of the first and/or second interaction region. In particular, the amino acids forming the covalent interaction pair may be part of the targeting region.

The amino acid sequence of the targeting region may be any sequence that is recognized or binds to a target molecule, in particular a cellular receptor. Non-limiting examples of such peptides are Lyp-1 (SEQ ID NO: 1), RGD (SEQ ID NO: 60, RGD), RGR, HER2 binding peptide (SEQ ID NO: 2), CREKA peptide (SEQ ID NO: 3), NGR peptide, CPP-2 (SEQ ID NO: 4), CPP-44 (SEQ ID NO: 5), F3 (SEQ ID NO: 6), RMS-P3 (SEQ ID NO: 7), F56 (SEQ ID NO: 8), LTVSPWY-peptide (SEQ ID NO: 9), WNLPWYYSVSPT-peptide (SEQ ID NO: 10), SP5-2 (SEQ ID NO: 11), heparan sulfate targeting peptide (SEQ ID NO: 61, CKNEKKNKI-ERNNKLKQPP), CGKRK-peptide (SEQ ID NO: 62, CGKRK), CSRPRRSEC-peptide (SEQ ID NO: 63, CSR-PRRSEC), CREAGRKAC-peptide (SEQ ID NO: 64, CREAGRKAC), CAGRRSAYC-peptide (SEQ ID NO: 65, CAGRRSAYC), RMS-P3 (SEQ ID NO: 66, CMGTINTRT-KKC), CKAAKN-peptide (SEQ ID NO: 67, CKAAKN), CSNRDARRC-peptide (SEQ ID NO: 68, CSNRDARRC), CGNSNPKSC-peptide (SEQ ID NO: 69, CGNSNPKSC), CSRESPHPC-peptide (SEQ ID NO: 70, CSRESPHPC), ASGALSPSRLDT-peptide (SEQ ID NO: 71, ASGAL- SPSRLDT), IL-4-receptor binding peptide (SEQ ID NO: 72, CRKRLDRNC), and PSP1 (SEQ ID NO: 73, CLSYYPSYC).

Thus, according to one embodiment of the first aspect of the invention, the targeting region comprises a sequence selected from the group consisting of SEQ ID NO: 1, RGD, RGR, SEQ ID NO: 2, SEQ ID NO: 3, NGR peptide, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or SEQ ID NO: 73. Preferably the amino acid sequence of the targeting region comprises SEQ ID NO: 1. In another preferred embodiment, the amino acid sequence of the targeting region comprises SEQ ID NO: 60.

Lyp-1 is a tumor homing peptide that selectively binds the tumor-associated lymphatic vessels and tumor cells in certain tumors. The nine amino acid long peptide specifically recognizes the receptor P32. The RGD-peptide and NGR-peptide are tri-peptides composed of L-arginine-glycine-L-aspartic acid and L-asparagine-glycine-L-arginine, respectively. The sequences are common elements in cellular recognition. RGD peptides are implicated in cellular attachment via integrins. The HER2 binding peptide specifically targets the Human Epidermal Growth Receptor 2 (HER2). The CREKA peptide is a tumor homing peptide identified in phage display libraries consisting of the sequence Cys-Arg-Glu-Lys-Ala (see Simberg D, et al. Biomimetic amplification of nanoparticle homing to tumors. Proc Natl Acad Sci USA. 2007 Jan. 16; 104(3):932-6). CPP-2 and CPP-44 are tumor homing peptides described in Kondo et al. Tumour-lineage-homing cell-penetrating peptides as anticancer molecular delivery systems. Nat Commun. 2012 Jul. 17; 3:951. F3 comprises amino acid sequences 17-48 of High Mobility Group Nucleosomal Binding Protein 2 (HMGN2) and was identified in a phage display cDNA library screen for peptides capable of homing to tumors, especially to their vascular endothelium (see (see Christian et al., Nucleolin expressed at the cell surface is a marker of endothelial cells in angiogenic blood vessels. J Cell Biol. 2003 Nov. 24; 163(4):871-8). RMS-P3 is a furin targeted peptide suitable for targeting Rhabdomyosarcoma (RMS) cells (see Hajdin K, et al. Furin targeted drug delivery for treatment of rhabdomyosarcoma in a mouse model. PLoS One. 2010 May 3; 5(5)). F56 specifically binds to VEGF receptor Flt-1 (see Herringson and Altin, Effective tumor targeting and enhanced anti-tumor effect of liposomes engrafted with peptides specific for tumor lymphatics and vasculature. Int J Pharm. 2011 Jun. 15; 411(1-2):206-14). LTVSPWY-peptide and WNLPWYYSVSPT-peptide specifically bind to breast cancer cells (see Shadidi and Sioud, Identification of novel carrier peptides for the specific delivery of therapeutics into cancer cells, FASEB J. 2003 February; 17(2):256-8). SP5-2 specifically binds to non-small cell lung cancer (see Chang D K, et al. A Novel Peptide Enhances Therapeutic Efficacy of Liposomal Anti-Cancer Drugs in Mice Models of HumanLung Cancer, PLoS ONE 2009 (1): e4171).

According to one embodiment of the first aspect of the invention, the loop between the first and second interaction region which comprises the targeting region has a number of amino acids in the range from 3 to 50 amino acids. The number of amino acids of the loop is counted from the covalent interaction pair "closing" the loop and consequently includes the amino acids of the covalent interaction pair. Accordingly a number of loop amino acids of 2 only includes the covalent interaction pair. Thus, the minimal number of amino acids in the loop is 3. The maximum length of the loop is in principle limited by the influence of the peptide on the folding of the fusion protein and the tendency for aggregation with higher length. Thus, the maximum number of amino acids in the loop is preferably 25, more preferably 20, most preferably 15 amino acids. According to a particularly preferred embodiment, the number of amino acids in the loop is in the range from 5 to 15 amino acids.

The covalent interaction pair may be formed by any two amino acids, the side chains of which may form a covalent bond. These may be in particular cysteines or seleno cysteines which form disulfide bridges. According to one embodiment of the first aspect of the invention, the covalent interaction pair is formed by a cysteine in the first interaction region and by a cysteine in the second interaction region. A fusion protein according to the invention may comprise more than one covalent interaction pair. For example, the fusion protein according to the invention may comprise 7 or less, 6 or less, 5, or less, 4 or less, 3 or less, 2 or less interaction pairs. The covalent interaction pairs may be located in sequence or spaced apart. Preferably, the fusion protein according to the invention comprises one covalent interaction pair.

According to one embodiment of the first aspect of the invention, at least two interaction pairs are non-covalent interaction pairs in which the amino acids interact non-covalently. Preferably, the second peptide comprises at least 3 non-covalent interaction pairs, more preferably at least 4 non-covalent interaction pairs. In principal, the higher the number of interaction pairs, the stronger the interaction of the first and second interaction region of the second peptide. The number of non-covalent interaction pairs also depends on the type of interaction of the amino acids. The non-covalent interaction may be by hydrogen bridges, van der Waal forces, hydrophobic interactions or acid-base interactions.

Preferably, at least a part of the non-covalent interaction pairs are acid-base interaction pairs formed by an acidic amino acid in one interaction region and a basic amino acid in the other interaction region. At a neutral pH, these amino acids are charged negatively and positively, respectively. The contrary charges of the amino acids lead to an attraction of these amino acids and consequently of the interaction regions. Moreover, the contrary charges provide a tight binding of binding.

According to one embodiment, the second peptide comprises 2 to 20 acid-base interaction pairs, preferably 2 to 10 acid-base interaction pairs, more preferably 2 to 6 acid-base interaction pairs, most preferably 3 to 5 acid-base interaction pairs. The higher the number of acid-base interaction pairs, the higher the attraction of the first and second interaction region. However, a number more than 20 acid-base interaction pairs will be problematic for the folding of the fusion protein. A number of more than 10 acid-base interaction pairs renders cloning more problematic as very long primers have to be used. Moreover, it is assumed that the use of more than 6 acid-base interaction pairs does not further significantly increase the interaction of the first and second interaction region. With regard to ease of cloning and optimal strength of interaction of the non-covalent interaction pairs, a number of 3 to 5 acid-base interaction pairs are preferred. In a particularly preferred embodiment of the first aspect of the invention the second peptide comprises 4 acid-base interaction pairs.

Basic amino acids according to the invention can be arginine, lysine or histidine. Acidic amino acids according to the invention can be glutamic acid or aspartic acid.

The first and second interaction region may comprise both acidic and basic amino acids, only acidic amino acids or only basic amino acids. The basic and acid amino acids in one interaction region may be alternating or form clusters. Non-limiting examples of alternating sequences are: EERR (SEQ ID NO: 45), ERER (SEQ ID NO: 46), EERREE (SEQ ID NO: 47), RREERR (SEQ ID NO: 48). Examples of clusters are EEERRR (SEQ ID NO: 49), DDERKK (SEQ ID NO: 50), DDDRR (SEQ ID NO: 51). However, it is preferred that one of the interaction regions comprises a majority of acidic amino acids and the other, consequently, a majority of basic amino acids. For example, the first interaction region comprises the mainly basic sequence RRRRE (SEQ ID NO: 52) and the second interaction region comprises the mainly acidic sequence EEEER (SEQ ID NO: 53).

According to a preferred embodiment of the first aspect of the invention, the non-covalent interaction pairs are acid-base interaction pairs and formed by an acidic amino acid in the first interaction region and basic amino acid in the second region. The first interaction region may comprise at least 2, at least 3, at least 4, at least 5, at least 6 acidic amino acids. Also, the second interaction region may comprise at least 2, at least 3, at least 4, at least 5, at least 6 basic amino acids. Preferably, the first interaction region comprises at least 4 acidic amino acids and the second interaction region comprises at least 4 basic amino acids. More preferably, the first interaction region comprises at least 4 consecutive acidic amino acids and the second interaction region comprises at least 4 consecutive basic amino acids.

According to one embodiment of the first aspect of the invention, the majority of the basic amino acids are arginine. In an alternative embodiment, the majority of the basic amino acids are lysines. Preferably, all basic amino acids in the interaction region are arginines.

The charged amino acids in the interaction regions, i.e. the acidic and basic amino acids of the first and second interaction region may be directly in sequence or contain non-charged amino acids as spacers in between. Accordingly, two charged amino acids in the interaction region may be directly connected or may be separated by one or more non-charged amino acids. The non-charged amino acids as spacer between the charged amino acids are preferably selected from the group consisting of serine and glycine. The number of non-charged amino acids, i.e. the spacing, between two charged amino acids may be for example 0, 1, 2, 3 or 4. According to one embodiment of the invention, the spacing of the charged amino acids within the amino acid sequence of the first interaction region is 0 or 1. According to one embodiment of the invention the spacing of the charged amino acids in the second interaction region is 0 or 1. According to one embodiment the spacing of the charged amino acids in the first and/or second interaction region is preferably 0. Thus, the charged amino acids in the first and/or second interaction region are directly connected.

In a preferred embodiment, the first interaction region comprises four consecutive arginines. According to one embodiment of the first aspect of the invention, the majority of the acidic amino acids are glutamic acids. According to an alternative embodiment, the majority of acidic amino acids are aspartic acids. Preferably, all acidic amino acids in the second peptide are glutamic acids. In particular the first interaction region comprises the sequence EEEE (SEQ ID NO: 54) and the second interaction region comprises the sequence RRRR (SEQ ID NO: 55). In a further preferred embodiment, the fusion protein comprises a first interaction region comprising the sequence RRRRSGC (SEQ ID NO: 74) and a second interaction region comprising the sequence CSGEEEE (SEQ ID NO: 75) as depicted in FIG. 1A. In a further preferred embodiment, the fusion protein comprises a first interaction region comprising the sequence RRRRC (SEQ ID NO: 76) and a second interaction region comprising the sequence CEEEE (SEQ ID NO: 77) as depicted in FIG. 1B.

According to one embodiment the first interaction comprises the sequence EGEGEGE (SEQ ID NO: 56) and the second interaction region comprises the sequence RGRGRGR (SEQ ID NO: 57). According to the one embodiment the first interaction comprises the sequence ESESESE (SEQ ID NO: 58) and the second interaction region comprises the sequence RSRSRSR (SEQ ID NO: 59).

The spacing region between the covalent interaction pair or pairs and the non-covalent interaction pair or pairs has an influence on the formation of the hair pin-like structure of the second peptide. If the number of amino acids forming the spacer is too high, the effect of bringing the amino acids of the covalent interaction pair proximity by means of the binding of the one or more non-covalent interaction pairs may be lost. In contrast, a too short distance may be problematic for steric reasons. For example, the size of the side chains of the acidic and basic amino acids is bigger than the size of the side chain of cysteines. Accordingly, if the cysteines are directly adjacent to the charged amino acids in the second peptide a disulfide bridge might not form. Thus, according to one embodiment of the first aspect of the invention, the number of amino acids in the first and second interaction region between the at least one covalent interaction pair and the closest non-covalent interaction pair is in the range from 1 to 6, preferably 1 to 4, more preferably 1 to 3. Most preferably, the spacers in both interaction regions between the at least one covalent interaction pair and the closest non-covalent interaction pair is 2 amino acids.

In addition, the type of amino acids forming the spacer between the at least one covalent interaction pair and the closest non-covalent interaction pair influences the formation of the covalent bond. For the spacers, polar uncharged amino acids, with short side chains are preferred such as glycine, serine or alanine. More preferably the amino acids of the spacers between the at least one covalent interaction pair and the closest non-covalent interaction pair are glycine and serine. According to a particularly preferred embodiment of the invention, the spacers between the covalent interaction pair and the non-covalent interaction pair consist of one glycine and one serine.

According to one embodiment of the fusion protein the first interaction region is Lyp-1 interaction region 1 as defined by SEQ ID NO: 20. According to one embodiment of the fusion protein the second interaction region is Lyp-1 interaction region 2 as defined by SEQ ID NO: 21. According to one embodiment the amino acid sequence of the first interaction region is defined as Lyp-1 interaction region 1 and the amino acid sequence of the second interaction region is defined as Lyp-1 interaction region 2.

Preferably, the second peptide is introduced into a region of the first peptide that is not essential for folding so that the second peptide does not interfere with the folding of the first peptide. Moreover, it is preferred that the second peptide is introduced into a region of the first peptide that is located on the surface of the first peptide when folded. The skilled person knows how to determine suitable positions within an amino acid sequence. Suitable positions are preferably determined from crystal structures of the protein or related proteins. Preferably, the second peptide is located in a loop of the first peptide of the fusion protein. More preferably in a loop on the surface of the first peptide.

The second peptide is particularly useful as a targeting peptide for targeting virus-like particles (VLPs). VLPs may comprise cargo that is useful only in specific cell types or toxic and must therefore address only specific cell types. Accordingly, it is preferred that the first peptide is a protein forming the capsid of a VLP.

According to a preferred embodiment, the first peptide is a polyoma virus VP1. "VP1" or "virus protein 1" according to the invention refers to a protein which is identical to or derived from the natural VP1 of the JC virus, having the amino acid sequence according to SEQ ID NO: 12. A protein derived from the natural VP1 of the JC virus preferably has an amino acid sequence homology or identity with the amino acid sequence according to SEQ ID NO: 12 of at least 80%, of at least 85%, of at least 90%, of at least 95%, of at least 97%, of at least 98%, or of at least 99%, or with a sequence of at least 100 contiguous amino acids, preferably of at least 150, of at least 200, of at least 250, of at least 300 contiguous amino acids. Most preferably, the amino acid sequence homology or identity is calculated over the entire length of the natural JCV-VP1. The terms "VP1 derived from the natural VP1 of the JC virus" and "VP1 derived from JC virus" in particular also include VP1, which is identical to the natural VP1 of the JC virus. The term "VP" according to the invention also encompasses fractions and derivatives of the natural VP1, which are capable of assembling into VLP. Preferably, said fractions and derivatives of VP1 at least comprise amino acids 32 to 316 of the amino acid sequence according to SEQ ID NO: 9 or a derivative thereof. Having a homology or identity with the amino acid sequence from amino acid position 32:316 of SEQ ID NO: 9 of at least 80%, of at last 85%, of at least 90%, of at least 95%, of at least 97%, of at least 98%, or of at least 99%.

Preferably, the first peptide is a VP1 from JCV. According to X-ray crystallography analysis the folded VP1 (e.g. PDB entry 3NXD) contains three loops on the surface of the protein. Two of these loops, the DE-loop (aa 120-137) and the HI-loop (aa 262-272) are known to be eligible for the introduction of exogenous peptide structures as an exogenous structure introduced into the loop is accessible and in general does not interfere with folding of the VP1 protein. Thus, according to one embodiment, the second peptide is located in the DE-loop or the HI-loop of VP1. Preferably, the peptide is located between amino acid 120 and 137 (DE-loop) or 262 and 272 (HI-loop) of VP1. More preferably between amino acid 129 and 132 (DE-loop) or 265 and 268 (HI-loop) of VP1. In particular, the second peptide substitutes amino acid 267 of the HI-loop. As described below, different expression systems are suitable for the expression of the protein. According to a preferred embodiment, the fusion protein is expressed in *E. coli.*

According to one embodiment of the fusion protein the first peptide is a VP1 from JCV and the second peptide comprises the Lyp-1 peptide. According to one embodiment the first peptide is a VP1 from JCV and the second peptide comprises the amino acid sequence with a sequence homology or identity with the amino acid sequence according to SEQ ID NO: 13 of at least 95%. According to one embodiment the first peptide is a VP1 from JCV and the second peptide comprises a amino acid sequence according to SEQ ID NO: 13. According to one embodiment the first peptide is a VP1 from JCV, the second peptide comprises a amino acid sequence according to SEQ ID NO: 13 and the second peptide is integrated into the DE-loop of the VP1. According to one embodiment the first peptide is a VP1 from JCV, the second peptide comprises an amino acid sequence according to SEQ ID NO: 13 and the second peptide is integrated into the HI-loop of the VP1. The fusion protein may have an amino acid sequence with a sequence homology or identity with the amino acid sequence according to SEQ ID NO: 14 of at least 95%. Alternatively, the fusion protein may have an amino acid sequence with a sequence homology or identity with the amino acid sequence according to SEQ ID NO: 15 of at least 95%.

3. Virus-Like Particle

According to a second aspect, the invention provides a virus-like particle (VLP) which comprises at least one fusion protein according to a first aspect of the invention. Preferably, the VLP is a polyoma virus VLP and the first peptide of the fusion protein is a polyoma virus VP1.

Non-limiting examples for viruses of the polyoma family are: B-lymphotropic polyomavirus (formerly known as African green monkey polyomavirus, AGMPyV) (LPyV), Baboon polyomavirus 1 (SA12), Bat polyomavirus (formerly known as *Myotis* polyomavirus, MyPyV; BatPyV) BK polyomavirus (BKPyV), Bornean orang-utan polyomavirus (OraPyV1), Bovine polyomavirus (BPyV), California sea lion polyomavirus (SLPyV), Hamster polyomavirus (HaPyV), JC polyomavirus (JCPyV), Merkel Cell polyomavirus (MCPyV), Murine pneumotropic virus (formerly known as Kilham strain of polyomavirus, Kilham virus, K virus; MPtV), Murine polyomavirus (MPyV), Simian virus 40 (formerly known as Simian vacuolating virus 40; SV40), Squirrel monkey polyomavirus (SqPyV), Sumatran orang-utan polyomavirus (OraPyV2), Trichodysplasia spinuolsa-associated polyomavirus (TSPyV), Human polyomavirus 6 (HPyV6), Human polyomavirus 7 (HPyV7), KI polyomavirus (formerly known as Karolinska Institute polyomavirus, KIPyV), WU polyomavirus (formerly known as Washington University polyomavirus, (WUPyV), Avian polyomavirus (formerly known as Budgerigar Fledgling disease polyomavirus, BFPyV, APyV), Canary polyomavirus (CaPyV), Crow polyomavirus (CPyV), Finch polyomavirus (FPyV), Goose Hemorrhagic polyomavirus (GHPyV), Athymic rat polyomavirus (RatPyV), Baboon polyomavirus 2 (BPyV2), Cynomolgus polyomavirus (CyPV), *Gorilla gorilla* gorilla polyomavirus 1 (GggPyV1), Human polyomavirus 9 (HPyV9), Trichodysplasia spinulosa-associated polyomavirus (TSV) Mastomys polyomavirus (multimammate mouse—Mastomys species), Pan troglodytes verus polyomavirus 1a (PtvPyV1a), Pan troglodytes verus polyomavirus 2c (PtvPyV2c), Rabbit kidney vacuolating virus (RKV).

Preferably the VLP is derived from a human polyoma virus comprising Human polyomavirus 6 (HPyV6), Human polyomavirus 7 (HPyV7), Human polyomavirus 9 (HPyV9), BK polyomavirus (BKPyV), JC polyomavirus (JCPyV), Merkel Cell polyomavirus (MCPyV), KI polyomavirus (formerly known as Karolinska Institute polyomavirus, KIPyV), WU polyomavirus (formerly known as Washington University polyomavirus, (WUPyV), Trichodysplasia spinulosa-associated polyomavirus (TSV), human polyoma virus 10 (HPyV10), MW polyomavirus and MX polyomavirus. In a more preferred embodiment of the invention, the VLP is derived from the human polyoma virus JCV.

VLPs are multi-protein structures that mimic the organization and conformation of authentic native viruses but lack the viral genome.

The virus-like particle according to the invention is preferably derived from human polyomavirus. In the context of the invention, the term "from human polyomavirus" refers to a VLP with structural proteins that can be isolated or extracted from polyomaviruses or which can be generated by recombinant expression of a polyoma structural protein or a modified form of said structural protein.

The capsids of all polyomaviruses have a similar structural set-up including the proteins VP1, VP2, VP3, and agnoprotein. The icosahedral virus capsid is formed by 72 VP1 pentamers. In the center of each of the pentamers, facing to the inside of the capsid, a VP2 or VP3 protein is located. VP3 is identical to the C-terminal two-thirds of VP2. This shared region comprises inter alia the nuclear localization signal (NLS), the DNA-binding domain (DBD), and the VP1 interacting domain (VID).

"VP2" or "virus protein 2" according to the invention refers to a protein which is identical to or derived from the natural VP2 of the JC virus, having the amino acid sequence according to SEQ ID NO: 22. A protein derived from the natural VP2 of the JC virus preferably has an amino acid sequence homology or identity with the amino acid sequence according to SEQ ID NO: 22 of at least 80%, of at least 85%, of at least 90%, of at least 95%, of at least 97%, of at least 98%, or of at least 99%, or with a sequence of at least 100 contiguous amino acids, preferably of at least 150, of at least 200, of at least 250, of at least 300 contiguous amino acids. Most preferably, the amino acid sequence homology or identity is calculated over the entire length of the natural JCV-VP2.

"VP3" or "virus protein 3" according to the invention refers to a protein which is identical to or derived from the natural VP3 of the JC virus, having the amino acid sequence according to SEQ ID NO: 23. A protein derived from the natural VP3 of the JC virus preferably has an amino acid sequence homology or identity with the amino acid sequence according to SEQ ID NO: 23 of at least 80%, of at least 85%, of at least 90%, of at least 95%, of at least 97%, of at least 98%, or of at least 99%, or with a sequence of at least 100 contiguous amino acids, preferably of at least 150, of at least 200, of at least 250, of at least 300 contiguous amino acids. Most preferably, the amino acid sequence homology or identity is calculated over the entire length of the natural JCV-VP3.

With the integration of a fusion protein according to the first aspect of the invention, the VLP may be targeted to a cell of interest. Polyomavirus VLPs are formed up to 72 pentamers. Each of these pentamers consists of 5 copies of VP1. Preferably, at least one pentamer of the icosahedral VLP capsid is formed by 1 to 5 copies of the fusion protein of the first aspect of the invention. Pentamers of the VLP may comprise 1, 2, 3, 4 or 5 copies of the fusion protein according to the first aspect. As the pentamers form upon expression and are stable also upon disassembly of the VLP, recombinant expression of only the fusion protein in a host cell generally leads to the formation of pentamers with 5 copies of the fusion protein.

According to one embodiment of the second aspect of the invention the ratio of pentamers formed by the fusion protein and pentamers formed by other VP1 is at least 1:71, at least 1:35, at least 1:23, at least 1:17, at least 1:11, at least 1:8, at least 1:7, at least 1:5, at least 1:3 at least 1:2. In this regard other VP1 proteins are VP1 constructs that do not include a fusion protein according to the invention. Preferably the ratio is at least 1:5. The higher the number of the fusion protein according to the invention in a VLP the higher the chance that the VLP will interact with a cell type specific for the targeting region of the fusion protein. However, the integration of a peptide into the structure of the VP1 may interfere with assembly of the VLP. Thus, it is preferred that at least a fraction of the pentamers is formed by VP1 without a peptide insertion, preferably by a VP1 with a sequence identity of at least 90%, of at least 95%, of at least 97%, of at least 98%, or of at least 99% to SEQ ID NO: 9.

The VLP according to the second aspect of the invention may comprise more than one type fusion protein according to the first aspect of the invention. For example, the VLP may comprise one type of fusion protein with a targeting region specific for a first target and a second type of fusion protein with a targeting region specific for a second target. Such a VLP is able to target to different targets. The two targets may for example be epitopes located on different cell types. Accordingly, at least two different types of cells can be targeted. Alternatively, the two targets may be located on one type of cells. In this scenario the two targeting regions increase the chance of affecting the specific cell type by the VLP. The VLP with more than one fusion protein according to the first aspect of the invention may comprise a first fusion protein with the Lyp1-peptide as targeting region and a second fusion protein with the LTVSPWY-peptide as targeting region. The VLP with more than one fusion protein according to the first aspect of the invention may further comprise a first fusion protein with the Lyp1-peptide as targeting region and a second fusion protein with the F3-peptide as targeting region. This VLP is particularly useful for targeting breast tumor cells. Moreover, the VLP with more than one fusion protein according to the first aspect of the invention may comprise a first fusion protein with the SP5-2-peptide as targeting region and a second fusion protein with the F3-peptide as targeting region.

The VLP according to the second aspect may further comprise minor capsid proteins such as VP2, VP3 or agno protein. The VLP preferably comprises a fusion protein comprising a VP1 binding protein, which preferably comprises the VP1 interacting domain of VP2 and an exogenous peptide, preferably selected from a cargo binding peptide (CBP) and endosomal translocating peptide (ETP).

According to one embodiment of the second aspect, the VLP comprises a second fusion protein comprising a VP1 binding protein and an exogenous peptide, wherein the exogenous peptide comprises a cargo-loading peptide and/or an endosomal translocating peptide (ETP).

The term "VP1 binding protein" refers to any peptide that has the ability to bind to the major capsid protein VP1 of a polyomavirus. In particular, the VP1 binding protein is a peptide comprising the VP1 interacting domain (VID) of a polyomavirus VP2/VP3 protein.

The VID may be derived from a VP2 or VP3 or differently termed functional equivalent thereof from any known polyomavirus.

The VP1 binding protein according to the invention comprises the VP1 interacting domain of VP2 and allows a positioning of the fusion protein and, in particular, the exogenous peptide within a VLP derived from a polyomavirus. Preferably, the VP1 interacting domain has an identity of at least 90%, preferably at least 95%, more preferably at least 98% to SEQ ID NO: 24. Thus, the VP1 binding protein preferably comprises at least a sequence with an identity of at least 90%, preferably at least 95%, more preferably at least 98% to SEQ ID NO: 24.

The VP1 binding protein is preferably a full length polyomavirus VP2 or VP3. These proteins are naturally adapted for the interaction with the VP1. Accordingly, in one embodiment of the first aspect of the invention, the VP1 binding protein comprises an amino acid sequence that has an identity of at least 80%, preferably at least 90%, more preferably at least 95% to SEQ ID NO: 22 or SEQ ID NO: 23.

However, any fragment or sub-structure of VP2 or VP3 may be sufficient for a tight interaction with VP1 as long as it contains a functional VP1 interacting domain of VP2/VP3. For example, the VP1 binding protein according to the invention may include or exclude the DNA-binding domain. For example, the VP1 binding protein may comprise the VID and the NLS of VP2. Further examples are a VP1 binding protein comprising the VID and the NLS of VP2, a VP1 binding protein comprising the VID and the DBD of VP2, and VP1 binding protein comprising the VID, DBD and the NLS of VP2.

The VP1 binding protein may be a modified version of VP2 or VP3, e.g. mutated by insertion, deletion, or amino-acid replacement with respect to SEQ ID NO: 22 or 23. However, the VP1 binding protein may only be modified to the point that the VP1 interacting domain is still functional, i.e. still binds to a polyomavirus VP1.

The exogenous peptide may be located at any position of the second fusion protein, i.e. at the C-terminus, at the N-terminus, or at any position within the amino acid sequence of the fusion protein. The location of the exogenous peptide is preferably on the surface of the folded protein. The exogenous peptide is further preferably freely accessible when the second fusion protein is bound to the VLP capsid. The skilled person knows how to determine positions within the amino acid sequences that fulfill these prerequisites. The structure predictions of VP2 or VP3 show that the N-terminus and the C-terminus are located on the surface of VP2 and VP3, and oriented to the inside of the polyoma virus when VP2 or VP3 is bound to a VP1 pentamer.

In one embodiment of the second aspect of the invention the exogenous peptide forms the C-terminus or the N-terminus of the second fusion protein. A second fusion protein containing the exogenous peptide on the C-terminus or N-terminus of the protein has the further advantage of an easier construction of the polynucleotide encoding the fusion protein. The C-terminus is particularly preferred as the location for the exogenous peptide because it is the part of the protein that is the last to be translated. Thus, an exogenous peptide on the C-terminus has the lowest influence on protein folding. According to one embodiment of the first aspect, the endosomal translocating peptide, preferably the CPP, is located on the C-terminus of the protein. Alternatively, the endosomal translocating peptide, preferably the CPP, forms the N-terminus of the second fusion protein. According to an alternative embodiment, the cargo loading peptide, in particular the cargo binding peptide, forms the C-terminus of the second fusion protein. Alternatively, the cargo binding peptide may form the C-terminus.

The exogenous peptide preferably has a percentage of basic amino acids of at least 25%, more preferably of at least 30%.

According to one embodiment of the first aspect of the invention, the exogenous peptide comprises a cargo loading peptide. A cargo loading peptide according to the invention is a peptide that affects the packaging of cargo in a VLP such that the cargo is better protected from the surrounding of the VLP in particular in the blood plasma or inside a cell.

Preferably the cargo loading peptide is a cargo-binding peptide. Depending on the application of the VLP it may be used for transporting different types of cargo. Examples of cargo are single- or double-stranded DNA, single- or double-stranded RNA, peptides, hormones, lipids, carbohydrates, or other small organic compounds. Further examples of cargos are chemotherapeutics such as alkylating agents (e.g. cyclophosphamide, calicheamicin), antimetabolites (e.g. 5-fluorouracil, methotrexate), anthracyclines (e.g. doxorubicin, epirubicin), RNA polymerase inhibitors (e.g. alpha-amanitin), or cytoskeletal drugs (e.g. colchicine, cytochalasin, demecolcine, latrunculin, jasplakinolide, nocodazol, taxanes, phalloidin, swinholide, vinca alkaloids). A preferred chemotherapeutic is the taxane Paclitaxel (Taxol). Chemotherapeutics may also be small organic compounds. Accordingly, the cargo-binding peptide may be specific for one or more of these possible cargos. A preferred cargo-binding peptide is a DNA-binding peptide. A further preferred cargo-binding peptide is an RNA-binding peptide.

As shown in the examples, a cargo-loading peptide fused to the VP2 or VP3 protein leads to an improved protection, i.e. less degradation, of DNA packaged into VLPs. Without being bound to theory, one explanation for this better protection of the DNA cargo is a tighter packaging of the VLP due to the improved interaction with the cargo. Accordingly, the cargo-loading peptide is in particular a cargo binding peptide. Wildtype polyomavirus VP2/VP3 already contain a DNA-binding domain located at the C-terminus. However, the addition of protamine-1 to the C-terminus VP2 or VP3 leads to an improved protection of the cargo with respect to the wild type VP2 or VP3.

The length of the cargo-binding peptide is in principle only limited by the requirement that it does not interfere with the folding of the fusion protein. However, the cargo-binding peptide preferably has a length in the range from 5 to 100 amino acids, more preferably in the range from 10 to 70 amino acids, most preferably in the range from 10 to 60 amino acids. In one embodiment, the length is in the range from 15 to 25 amino acids.

According to one embodiment of the second aspect of the invention, the amino acid sequence of the cargo-binding peptide has a percentage of basic amino acids of at least 40%. Basic amino acids are positively charged. The positive charge facilitates a binding to negatively charged cargo, e.g. nucleotides. Preferably, the majority of the basic amino acids of the cargo-binding peptide are arginine residues. Accordingly, the percentage of arginine residues in the sequence of the cargo-binding peptide is at least 20%, more preferably at least 25%, most preferably at least 35%. In a particularly preferred embodiment, the percentage of arginine is at least 40%.

According to one embodiment of the cargo-binding peptide comprises a structural motif $(R)_n$ wherein n is an integer of at least 2, at least 3, at least 4, at least 5.

Cargo-binding peptides according to the invention may be DNA-binding peptides, RNA-binding peptides, peptide-binding peptides, lipid-binding peptides, carbohydrate-binding peptides. Examples of such peptides are protamine-1 (PRM1), Snap tag, SAMp73 Preferably, the CBP in the fusion protein according to the invention is protamine-1. Besides cargo-binding peptides the group of cargo-loading peptides also includes for example GFP or EGFP. According to one embodiment of the fusion protein according to the first aspect of the invention the cargo-loading peptide is neither GFP nor EGFP.

According to a further embodiment of the second aspect of the invention the amino acid sequence of the cargo-loading peptide has an identity of at least 80%, preferably of at least 90%, more preferably of at least 95% to SEQ ID NO: 25 (Protamine-1) or SEQ ID NO: 26(Protamine-1aa8-29). A sequence identity to SEQ ID NO: 25 is particularly preferred. As shown in the examples, protamine-1 bound to either VP2 or VP3 has a strong effect on the protection of the cargo transported by VLPs.

According to an alternative embodiment of the second aspect of the invention the exogenous peptide comprises an endosomal translocating peptide (ETP).

An "ETP" according to the invention is a peptide that has the ability to translocate itself and any cargo bound to it through the endosomal membrane. Preferred endosomal translocating peptides are in particular cell-penetrating peptides (CPP). Cell-penetrating peptides (CPPs) are short peptides that facilitate cellular uptake of various molecular cargo (from nano-size particles to small chemical molecules or large fragments of DNA). The cargo is associated with the peptides either through chemical linkage via covalent bonds or non-covalent interactions. The functions of the CPPs are to deliver the cargo into the cells. A process that commonly occurs through endocytosis with the cargo delivered to the endosomes of the living mammalian cells. However, other peptides not classified as CPPs have the same function providing means to translocate through the endosomal membrane. Such peptides are also included in the definition of ETPs. One example for such a peptide is a polyhistidine peptide. A polyhistidine peptide consists of at least six histidine (His) residues. It was shown that a polyhistidine peptide also has a destabilizing effect on membranes. According to one embodiment of the first aspect of the invention the ETP is not a $His_6$-tag.

CPPs typically have an amino acid composition that either contains a high relative abundance of positively charged amino acids such as lysine or arginine, or has sequences that contain alternating pattern of charged amino acids and non-polar/hydrophobic amino acids. These two types of structures are referred to as polycationic or amphiphatic, respectively. A third class of CPPs are hydrophobic peptides, containing only apolar residues with a low net charge or have hydrophobic amino acid groups that are crucial for cellular uptake.

The mechanism by which the CPPs translocate the plasma membrane and facility the delivery of molecular cargo to the cytoplasm or an organelle is not entirely understood. However, the theories of CPP translocation can be classified into three main entry mechanisms: direct penetration in the membrane, endocytosis-mediated entry, and translocation through the formation of a transitory structure.

The CPP is in theory not limited in length; however, the peptide must allow a correct folding of the fusion protein. The cargo-binding peptide preferably has a length in the range of 5 to 100 amino acids, more preferably in the range from 10 to 30 amino acids, most preferably in the range from 15 to 25 amino acids.

Preferably, the CPPs contain in addition to the basic amino acids also non-polar amino acids. In particular, the CPP has a percentage of non-polar amino acids of at least 25%, preferably of at least 30%, more preferably of at least 35%. The groups of CPPs differ in their relative percentage of basic non-polar amino acids.

The first type of CPPs, the amphipathic CPPs consist of alternating basic and non-polar amino acids. The amphipathic form often generates a pore or channel through the membrane bilayer. Examples of amphipathic CPPs are the trans-activating transcriptional activator (TAT) from human immunodeficiency virus-1 (HIV-1) and penetratin, a peptide derived from the DNA-binding domain of antennapedia homeo protein. The second type of CPPs, the so-called polycationic CPPs include the HPV peptide L2. These CPPs comprise at least one cluster of basic amino acids adjacent to at least one cluster of hydrophobic amino acids. Both regions are required for full activity of the peptide. Without being bound to theory, scientific results suggest that the positive charge of the basic amino acid cluster mediates tight association with negatively charged lipids of the membranes and that subsequent insertion of the hydrophobic duster into membranes induces a torsional stress which results in membrane disruption.

Amphipathic CPPs in particular have a percentage of basic amino acids in the range from 40 to 60%, and a percentage of non-polar amino acids in the range from 28 to 39%. The amphipathic CPPs preferably have a percentage of arginines in the range from 18 to 36%, and a percentage of lysines in the range from 22 to 28%.

The polycationic CPPs preferably have a percentage of arginines in the range from 26 to 30%, and a percentage of lysines in the range from 3 to 8%.

According to one embodiment of the first aspect of the invention, the amino acid sequence of the CPP comprises a structural motif $(R)_n$, wherein $n$ is an integer of at least two, preferably of at least three, more preferably of at least four, and the sequence further comprises two or more adjacent non-polar amino acids. Polycationic CPP, such as HPV 33-L2, may have a sequence of four arginines and a sequence of three non-polar amino acids.

Preferred CPPs according to the invention are TAT, penetratin, and HPV 33-L2. TAT has an amino acid sequence as defined by SEQ ID NO: 27. Penetratin has an amino acid sequence as defined by SEQ ID NO: 28, and HPV 33-L2 has an amino acid sequence as defined by SEQ ID NO: 29. A further preferred CPP is a variant of HPV 33-L2, which is identified as HPV 33-L2-DD447 (SEQ ID NO: 30), differs from HPV 33-L2 by a replacement of the N-terminal phenylalanine and isoleucine by two aspartates. This variant was shown to have a stronger cell-penetrating effect (Kemper et al., 2006). Further examples of CPPs according to the invention are SynB1 (SEQ ID NO: 31), SynB3 (SEQ ID NO: 32), PTD-4 (SEQ ID NO: 33), PTD-5 (SEQ ID NO: 34), FHV Coat-(35-49) (SEQ ID NO: 35), BMV Gag-(7-25) (SEQ ID NO: 36), HTLV-II Rex-(4-16) (SEQ ID NO: 37), D-Tat (SEQ ID NO: 38), R9-Tat (SEQ ID NO: 39).

Thus, according to one embodiment of the first aspect of the invention, the amino acid sequence of the CPP has an identity of at least 80%, preferably of at least 90%, more preferably of at least 95%, most preferably of at least 98% to SEQ ID NO: 27. Alternatively, the amino acid sequence of the CPP has an identity of at least 80%, preferably of at least 90%, more preferably of at least 95%, most preferably of at least 98% to SEQ ID NO: 28. The sequence of the CPP may also have an identity of at least 80%, preferably of at least 90%, more preferably of at least 95%, most preferably of at least 98% to SEQ ID NO: 29. Moreover, the amino acid sequence of the CPP may have an identity of at least 80%, preferably of at least 90%, more preferably of at least 95%, most preferably of at least 98% to SEQ ID NO: 30.

According to one embodiment of the first aspect of the invention, the fusion protein comprises at least one exogenous cargo-binding peptide, and at least one exogenous CPP. That way, the fusion protein may provide to a VLP, which is used as a transport system for a specific cargo into a cell, a tighter packaging, an improved protection of the cargo, and, in addition, an improved ability to leave the endosomal pathway and arrive at the cytoplasm. Consequently, the combination of an ETP, in particular a CPP, and a cargo-loading peptide, in particular a cargo-binding peptide together in one fusion protein with the ability to bind to the major structural protein VP-1 strongly increases the yield of cargo entering the cytoplasm of a cell and thus increases the efficiency of a VLP mediated transport into a cell.

In a fusion protein comprising both a cargo-binding peptide and a CPP, the two peptides may be located at opposite termini of the fusion protein. Thus, either the cargo-binding peptide forms the N-terminus of the fusion protein, and the CPP forms the C-terminus of the fusion protein, or the cargo-binding peptide forms the C-terminus of the fusion protein and the CPP forms the N-terminus of the fusion protein. Both termini of VP2 and VP3 are presented to the surface of the protein and to the inside of the VLP when the VP2/VP3 is attached to VP1. VP2 and VP3 both contain a DNA-binding sequence on the C-terminus of the peptide. Thus, preferably, the exogenous cargo-binding peptide forms the C-terminus of the fusion protein and the CPP forms the N-terminus of the fusion protein.

According to one embodiment of the second aspect of the invention, one exogenous peptide comprises the CPP and the cargo-binding peptide and forms the N- or C-terminus of the protein. A localization of the two peptides on the C-terminus is preferred. The localization on the C-terminus is advantageous in cases in which the exogenous peptide may interfere with the protein folding. As protein folding already occurs co-translationally, there will be less interference by an exogenous peptide bound to the C-terminus which is only translated in the end.

It is preferred that the first peptide of the fusion protein comprises VP1 from the same polyomavirus as the further VP1 proteins forming the VLP.

According to one embodiment of the second aspect of the invention, the VLP comprises no cargo. In the context of this invention, a VLP without cargo is also referred to as "empty VLP". Preferably, the empty VLP comprises a second fusion protein according to the invention wherein the VP1 binding protein is VP2.

Surprisingly, it was found that an empty VLP can be designed that exhibits cytotoxic properties when introduced into a cell. An example of a cytotoxic empty VLP is VLP comprising a second fusion protein according to the invention wherein the VP1 binding protein is VP2. Due to the cytotoxic effect this empty VLP may for example be used as chemotherapeutic agents. The cytotoxic effect is preferably cell specific. A high cell specificity of the cytotoxic effect has the advantage that only specific cell types can be targeted in order not to harm any healthy cells. Thus, an empty VLP preferably comprises targeting means for specific cells on which the cytotoxic effect should be acted on. This targeting means is provided by a fusion protein according to the first aspect.

According to an alternative embodiment of the second aspect of the invention, the VLP comprises a cargo. Non limiting examples of cargo are single-stranded or double-stranded DNA, single-stranded or double-stranded RNA, peptides, hormones, lipids, carbohydrates, or other small organic compounds or mixtures thereof. Further examples of cargos are chemotherapeutics, such as alkylating agents (e. g. cyclophosphamide, calicheamicin), antimetabolites (e. g. 5-fluorouracil, methotrexate), anthracyclines (e. g. doxorubicin, epirubicin), RNA polymerase inhibitors (e. g. alpha-amanitin), or cytoskeletal drugs (e. g. colchicine, cytochalasin, demecolcine, latrunculin, jasplakinolide, nocodazol, taxanes, phalloidin, swinholide, vinca alkaloids). A preferred chemotherapeutic is the taxane Paditaxel (Taxol). Chemotherapeutics may also be small organic compounds. Preferably, the cargo is a substance that produces an effect in a eukaryotic cell, in particular a mammalian cell. A preferred type of cargo is a substance that is pharmaceutically active. Preferably, the cargo is a molecule able to act on RNA. More preferably, the cargo is siRNA. In another preferred embodiment, the cargo is a chemotherapeutic.

According to one embodiment of the second aspect of the invention the VLP is for use as a medicament. In particular, the VLP is for use in the treatment of tumor diseases. In this regard the VLP provides a vehicle for the cargo, preferably a pharmaceutically active ingredient, to enter the cells of an organism. Thus, according to one embodiment the VLP is for use as a drug delivery system. For this purpose the VLP is loaded by a drug of interest. Loading drugs into VLP is especially useful for drugs which are too toxic to be delivered and/or too hydrophilic to enter cells on their own, for example chemotherapeutics. The loading of the drug is in particular performed by disassembly of the VLP into pentamers and reassembly in the presence of the cargo. The VLP drug delivery system is then used to deliver the loaded drug to a specific target.

In one embodiment according to the second aspect of the invention, the cargo is a pharmaceutically active substance that is not applicable by itself to a patient or leads to strong side effects. An example of a group of such substances is chemotherapeutic substances. According to a further embodiment, the cargo is a diagnostic agent. Preferably, the diagnostic agent is a substance used in imaging methods. More preferably, the diagnostic agent is a dye, in particular a fluorescent dye. Thus, according to one embodiment of the second aspect the VLP is used as a diagnostic method. Preferably the diagnostic method includes the visualization of metastases and/or tumors, in particular for the preparation of a surgery.

The treatment or diagnosis of a patient with a VLP according to the second aspect of the invention comprises the transfer of the cargo into a cell of an organism. Preferably, the organism is a mammal, more preferably, a human.

In one specific embodiment the VLP according to the invention are administered to the object in need thereof, in particular to humans, intravenously.

4. Pharmaceutical Composition

According to a third aspect, the invention provides a pharmaceutical composition that comprises at least one VLP according to the second aspect of the invention, and at least one pharmaceutically acceptable excipient.

5. Polynucleotide

According to a fourth aspect, the invention provides an isolated polynucleotide that comprises a nucleic acid sequence encoding a fusion protein according to the first aspect of the invention.

The techniques used to isolate or clone a polynucleotide encoding a peptide are known in the art and include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used.

The isolated polynucleotide preferably comprises a first part encoding first peptide and second part encoding the second peptide. The first part of the polynucleotide encoding the first peptide preferably has a degree of sequence identity to the JCV-VP1 coding sequence SEQ ID NO: 7 of at least 80 percent, at least 85 percent, at least 90 percent, at least 95 percent, at least 96 percent, at least 97 percent, at least 98 percent, at least 99 percent, or 100 percent. In one embodiment of the fourth aspect of the invention the first part of the polynucleotide encoding the VP1 binding protein hybridizes under very low stringency conditions, low stringency conditions, medium stringency conditions, medium-high stringency conditions, high stringency conditions, or very high stringency conditions with SEQ ID NO: 7.

According to one embodiment of the fourth aspect of the invention, the second part of the polynucleotide encoding the second peptide preferably has a degree of sequence identity to SEQ ID NO: 8 of at least 80 percent, at least 85 percent, at least 90 percent, at least 95 percent, at least 96 percent, at least 97 percent, at least 98 percent, at least 99 percent, or 100 percent, which encode a polypeptide having protease activity. Preferably, the second part of the polynucleotide encoding the second peptide preferably hybridizes under very low stringency conditions, low stringency conditions, medium stringency conditions, medium-high stringency conditions, high stringency conditions, or very high stringency conditions with SEQ ID NO: 8.

6. Expression Vector

In a fifth aspect the invention also relates to expression vectors comprising a polynucleotide according to the fourth aspect of the invention. The expression vector further preferably comprises control elements such as a promoter, and transcriptional and translational stop signals. The polynucleotide of according to the fourth aspect and of the control elements may be joined together to produce a recombinant expression vector that may include one or more restriction sites to allow for insertion or substitution of the polynucleotide encoding the polypeptide at such sites. The polynucleotide may be inserted into an appropriate expression vector for expression. In creating the expression vector, the coding sequence is located in the expression vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide of the fourth aspect of the invention. The choice of the expression vector will typically depend on the compatibility of the expression vector with the host cell into which the expression vector is to be introduced. The expression vectors may be a linear or closed circular plasmid.

The expression vector may be adapted for cell-based or cell-free expression. The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Alternatively, the vector may be one that, when introduced into the host cell, is integrated into the genome and replicated together with the chromosome(s) into which it has been integrated. For integration into the host cell genome, the expression vector may rely on any other element of the expression vector for integration into the genome by homologous or non-homologous recombination. Alternatively, the vector may contain additional polynucleotides for directing integration by homologous recombination into the genome of the host cell at a precise location in the chromosome.

The vectors of the present invention preferably contain one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

The procedures used to ligate the elements described above to construct the recombinant expression vectors of the present invention are well known to one skilled in the art (see, e.g., Sambrook et al., 1989, supra).

7. Host Cells

According to a sixth aspect the invention provides a host cell, comprising the expression vector according the fifth aspect of the invention. The expression vector according to the fifth aspect is introduced into a host cell so that the expression vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*. Preferably the host cell is *E. coli.*

The host cell may also be a eukaryote, such as a mammalian, insect, plant, or fungal cell. Preferably, the host cell is an insect cell, still more preferably a lepidopteran cell, and most preferably a cell selected from the group consisting of Sf9, Sf21, Express SF+, and BTITn-5B1-4 ("TN High Five").

8. Production Method

According to a seventh aspect the invention provides a process of producing the VLP according the second aspect of the invention.

The process at least comprises the steps of protein expression of the fusion protein according to the first aspect of the invention with a polynucleotide according to the fourth aspect of the invention as a template, purifying the fusion protein and assembling several copies of the fusion protein together with several copies of VP1 to form a VLP.

For expression of fusion protein cell-based or cell-free (in vitro) expression systems may be used. Common cell based systems are bacteria, such as *E. coli, B. subtilis*, yeast, such as *S. cerevisiae* or eukaryotic cell lines, such as baculovirus infected Sf9 cells mammalian cells like CHO or HeLa.

Cell-free (In vitro) protein expression is the production of recombinant proteins in solution using biomolecular translation machinery extracted from cells. Cell-free protein production can be accomplished with several kinds and species of cell extract. Extracts used for cell-free protein expression are made from systems known to support high level protein synthesis. For example cell-free extracts capable are made from *E. coli*, rabbit reticulocyte lysates (RRL), wheat germ extracts, or insects cell (such as SF9 or SF21) lysates.

Preferably, a cell based expression system is used. Thus, according to one embodiment of the sixth aspect of the invention the process of producing the VLP according the second aspect of the invention comprises at least the steps of:

a) introducing a polynucleotide according to the fourth aspect into a host cell;
b) culturing the transformed host cell in a medium under conditions leading to a protein expression with the nucleic acid as a template;
c) isolating the expression product from the cell; and
d) assembly of the expression product optionally with further viral proteins into the VLP.

Suitable host cells and expression vectors are described above. The use of baculo viruses together with insect cells, in particular SF9 cells, is preferred.

Methods of cultivation of host cells in a nutrient medium suitable for production of the fusion protein are well known in the art. For example, the host cell may be cultivated by shake flask cultivation, small-scale or large-scale fermentation (including continuous, batch, fed-batch, or solid state fermentations) in laboratory or industrial fermenters performed in a suitable medium and under conditions allowing the fusion protein to be expressed. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

Depending on the host/vector system used the fusion protein may or may not be secreted into the nutrient medium. In case it is secreted the polypeptide can be recovered directly from the medium. Otherwise the cells are separated from the culture medium and lysed.

Methods of cell lysis are known in the art. Non-limiting examples of the methods of cell lysis are mechanical disruption, liquid homogenization, sonication, freeze-thaw procedure or mortar and pestle.

The fusion protein may be recovered using methods known in the art. For example, the fusion protein may be recovered from the nutrient medium by conventional procedures including, but not limited to, centrifugation, filtration, extraction, spray-drying, evaporation, or precipitation.

The fusion protein may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

Expressed VP1 assembles into VLPs upon expression. The VLP may be disassembled by incubation with a reducing agent and a chelating agent (e.g. 5 mM EDTA). A preferred reducing agent is DTT. The concentration of DTT is preferably in the range from 1 to 30 mM, more preferably the concentration of DTT is in the range from 5 to 15 mM, in particular about 1 mM. The chelating agent is preferably EDTA. The concentration of EDTA is preferably in the range from 1 to 15 mM, more preferably the concentration of is in the range from 2 to 10 mM, in particular about 5 mM. Suitable incubation conditions are for example a temperature in the range from 20 to 30° C., preferably about 25° C. a duration of 20 min to 2 h, preferably about 1 h and a shaking speed in the range from 200 to 2000 rpm preferably about 1000 rpm.

Under these conditions the VLP disassembles into VP1 pentamers. The VP1 pentamers can for example be reassembled into icosahedral VLPs by dialysis against 2×2 liter reassembly buffer (10 mM TrisHCl pH 7.4; 150 mM NaCl; 2 mM $CaCl_2$) for at least 84 h. In order to produce a VLP with the fusion protein the fusion protein may be incubated with the VP1 pentamers during the disassembly procedure (see above). The fusion protein and VP1 pentamers than reassemble during dialysis into mixed VLPs.

According to one embodiment of the process further comprises the steps:

f) disassembly of the VLP into pentamers;
g) mixture of the pentamers with wildtype VP1 pentamers; and
h) reassembly of VLPs from the pentamer mixture.

An overview of the process is shown in FIG. 2.

The fusion protein according to the first aspect can for example be incorporated into the capsid envelope by co-expression of the respective fusion protein and VP1 in a suitable host cell e.g. a eukaryotic cell. In a preferred embodiment of the invention the fusion protein is co-expressed with a VP1 or a fusion protein comprising the VP1. In particular the fusion protein and the VP1 are coexpressed in Sf9 cells.

Active substances can be incorporated into the interior of the capsid envelope by for example dissociation of the capsid envelope and subsequent re-association in the presence of the active substance or by osmotic shock of the VLP in the presence of the active substance.

EXAMPLES

Example 1: Cloning of VLP-Variants with a Cyclic Lyp-1-Peptide in Via Whole Vector PCR a) Introduction of the cyclic Lyp-1-peptide into the HI-loop Primers:

```
Lyp-1peptid_HI-Loop FW
                                          (SEQ ID NO: 40)
GAACTAGAGGGTGCGGATCCGAAGAGGAAGAGGGTTCCCAGCAGTGG Lyp-1peptid_HI-Loop RV
                                          (SEQ ID NO: 41)
GCTTGTTACCACAACCTGATCTACGTCTACGGTTGGTGAACATGC
```

Plasmid:
pTXB1_VP1 (SEQ ID NO: 42)

Before the PCR the primers were phosphorylated 20 min at 37° C. and 10 min at 75° C. in the following reaction set up:

| | |
|---|---|
| 50 pmol | primer |
| 2 µl | buffer A |
| 2 µl | 10 mM dATP |
| 10 U | T4 polynucleotide kinase (Fermentas) |
| ad 20 µl | bidest H$_2$O. |

The following PCR mixture was prepared:

| | |
|---|---|
| 1.00 µl | pTXB1_VP1 (1 ng/µl) |
| 4.00 µl | 5x PCR Q5 Puffer (w 7.5 mM MgCl2) |
| 0.40 µl | 10 mM dNTP (200 µM) |
| 1.00 µl | Lyp-1peptid_HI-Loop_FW (10 µM) |
| 1.00 µl | Lyp-1peptid_HI-Loop_RV (10 µM) |
| 0.20 µl | Q5-Hot Start (2 U/µl NEB) (0.4 U) |
| 12.40 µl | H$_2$O MilliQ |

For PCR, the following temperature profile was used: An initial activation at 98° C. for 30 sec followed by 25 repetitions of the following cycle steps 1 to 3: 1) Denaturation: 98° C. for 10 seconds; 2) Annealing: 60° C. for 10 seconds; and 3) Extension: 72° C. for 3 min. After the temperature cycling, the samples were again kept at 72° C. for 10 min and finally cooled to 12° C. until the samples were retrieved.

PCR products (7771 bp) were separated by agarose gel electrophoresis and fragments of about 7400 bp were eluted using the QiaEx Kit (Qiagen).

Fragments were eluted with 30 µl of 70° C. buffer 4 (NEB) and subsequently incubated with 2 µl DpnI (digest of methylated template plasmid DNA) for 2 h at 37° C. followed by an additional 20 min at 80° C. for inactivation of the DpnI. Afterwards the PCR fragments were religated to using the T4 ligase.

Ligation Reaction Set Up:

| | |
|---|---|
| 2 µl | PCR-Product |
| 1 µl | 10x Ligase-buffer |
| 2.5 | Units Ligase |
| Ad 10 µl | ddH$_2$O |

For ligation the samples were incubated for 1 h RT.

The plasmids were then transformed into competent DH5α bacteria by thermal shock. Accordingly, 5 µl ligation sample were added to 50 µl competent XL1Blue cells and incubated for 30 min on ice, heated for 45 s at 42° C. followed by further incubation for 2 min on ice. Afterwards, 500 µl SOC were added and the cells were incubated for 30 min at 37° C. The cells were then harvested for 5 min at 3.000×g, the cell pellets resuspended in 50 µl SOC and 20 µl of the cell suspension spread on "amp+" agar plates.

Single colonies growing on the amp+ agar plate were tested for correct insertion. For this, the plasmid DNA was prepared by DNA Miniprep (Qiagen) according to the manufacturers' protocol. The obtained DNA was digested with the restriction enzyme AgeI. A construct with a correct insertion would yield two bands in agarose gel electrophoresis at 6703 base pairs and 1068 base pairs. Clones with correct restriction pattern were sequenced.

b) Introduction of the Cyclic Lyp-1-Peptide into the DE-Loop

For introduction of the Lyp-1-peptide into the DE-loop the protocol as described under a) was used with the following differences.
Primers:

Lyp-1peptid_DE-Loop_FW
(SEQ ID NO: 43)
GAACTAGAGGGTGCGGATCCGAAGAGGAAGAGGGTGCTGGCAAGC Lyp-1peptid_DE-Loop_RV
(SEQ ID NO: 44)
GCTTGTTACCACAACCTGATCTACGTCTACGGTGGGTAGCCTGGC The expected band size in the restriction analysis was 6760 base pairs and 1011 base pairs DE-Loop.

c) Introduction of the Cyclic RGD-Peptide into the HI-Loop

For introduction of the RGD-peptide into the HI-loop the protocol as described under a) was used with the following differences.

Primers:

```
cRGDpeptid_VP1-HI-Loop_FW
                                          (SEQ ID NO: 78)
GATTCATGCGGATCCGAAGAGGA cRGDpeptid_VP1-HI-Loop_RV
                                          (SEQ ID NO: 79)
ACCTCTACCACAACCTGATCTACGTCTAC
```

The plasmid template was pTXB1_VP1-HI-Loop-Lyp1, which is the resulting peptide from the protocol described under a) including the introduced Lyp1 peptide.

The PCR product had a size of 7765 bp.

The obtained DNA was digested with the restriction enzyme BamHI. A construct with a correct insertion would yield two bands in agarose gel electrophoresis at 6695 base pairs and 1070 base pairs. Clones with correct restriction pattern were sequenced.

Example 2: Expression and Purification of VP1-Lyp1 Fusion Proteins in *E. coli* a) Protein Expression

Expression vectors pTXB1_VP1-HI-Loop+Lyp1 and pTXB1_VP1-DE Loop+Lyp1 were produced according to Example 1.

For expression in *E. coli* the plasmids were transformed into the *E. coli* strain BL21 (DE3). For transformation, chemically competent cells were mixed with 1 ng of plasmids and incubated on ice for 30 min. Transformation was induced by heat shock for 45 s at 42° C. After this cells were transferred back to ice for at least 2 min before addition of SOC medium (37° C.) and incubation for 1 h at 37° C. under continuous shaking (225 rpm). For selection of positively transformed *E. coli* BL21 the culture was spread out on LB agar plates containing ampicillin (LB-amp) as selective marker. For expression, a colony grown on the LB-amp plate was inoculated into 50 ml LB medium comprising ampicillin in a concentration of 100 μg/ml and grown overnight at 37° C. and 225 rpm. This overnight culture was transferred into one liter LB-amp medium. Inoculated cultural medium was split into four 250 ml fractions and transferred into 1000 ml Erlenmeyer flasks. The four cultures were grown at a temperature of 37° C. with a shaking speed of 225 rpm until reaching an OD600 of 0.4. At this growth stage, protein expression was induced by an addition of 0.4 mM IPTG (end concentration). After induction of protein expression, the cells were grown for four hours at 30° C. with 225 rpm shaking.

b) Protein Preparation

Cells were harvested by centrifugation at 3,500 g and 4° C. for 15 minutes. The supernatant was discarded and the pellets were resuspended in 15 ml lysis buffer, joining two resuspended pellets in one 50 ml falcon tube.

Lysis Buffer
20 mM Tris-HCl, pH 8.5
500 mM NaCl
1 mM EDTA
1 mM TCEP
0.1% Triton-X 100

Lysozyme was added at a concentration of 20,000 units per milliliter of cell suspension. The cell suspension was then incubated for 30 minutes in an overhead shaker at 4° C. After incubation into each of the falcons, 5 g of silica beads (0.1-0.2 mm, Mühlmeyer) were added. The cells were lysed in a BigPrep adapter with the FastPrep instrument (MPBio) at 6.5 m/s for 30 seconds in two repetitions. The lysed cells were then centrifuged at 10,000 g and 4° C. for 15 minutes. The supernatants were recovered and stored for further processing. The pellets were then resuspended in 15 ml Lysis Buffer and lysed using the FastPrep system as described above. The cells were again centrifuged at 10,000 g and 4° C. for 15 minutes. The supernatants were retrieved and joined with the stored supernatants.

c) Protein Purification 10 ml of chitin agarose were filled into a column. The column was washed with 100 ml of Column Buffer and stored at 4° C.

Column Buffer
20 mM TrisHCL, pH 8.5
500 mM NaCl
1 mM EDTA

The supernatants of the protein preparation were again spun at 15,000 g at 4° C. for 30 minutes and afterwards applied onto the chitin column. The protein solution was allowed to pass the chitin column by gravity flow. After the protein solution has passed the column by gravity flow, the chitin column was washed with 200 ml column buffer by gravity flow. After the column buffer has run through, 30 ml cleavage buffer were added.

Cleavage Buffer
20 mM TrisHCl, pH 8.5
200 mM NaCl
1 mM EDTA
15 mM DTT

After the Cleavage Buffer has entered the gel, the chitin column was closed and incubated overnight at room temperature. After incubation, the cleavage buffer was removed by gravity flow. For elution, five 10 ml portions of elution buffer were added and let run through the column collecting the eluate.

Elution Buffer
20 mM TrisHCl, pH 8.5
200 mM NaCl
1 mM EDTA
2 mM DTT.

During the preparation and purification, samples were collected at the different steps and tested together with samples of the eluate using SDS-PAGE and Western d) Analysis of the Protein Production SDS-PAGE was performed with two gels containing the same samples. One gel was stained with InstantBlue. The second one was used for Western Blot analysis. The proteins were transferred from the gel to a membrane for one hour at 1 mA/cm$^2$. Afterwards, free protein binding sites on the membrane were blocked for 30 minutes at room temperature in PBS-T containing 5% (w/w) low fat milk powder. The low fat milk solution was removed and the first antibody AK 254 C7E4 diluted 1 to 5,000 in PBS-T plus 0.5% (w/w) low fat milk powder was added to the membrane and incubated for one hour at room temperature. After incubation, the membrane was incubated three times for five minutes in PBS-T. The PBS-T was removed and the second antibody was applied. For this, a goat anti-mouse POX was diluted 1 to 10,000 in PBS-T+0.5% low fat milk powder. The antibody solution was added to the membrane and incubated for one hour at room temperature. The membrane was again washed three times for 5 minutes in PBS-T. Bound secondary antibody was detected by chemoluminescence. Eluate fractions showing a positive signal were pooled and the volume was reduced by a factor of 10 using Viva spin 20 columns (molecular weight cut off 30,000). Protein content and purity of the final eluate were determined via an Experion analysis system (Biorad).

Example 3: Expression of VP1 in Sf9 and Production of VLP a) Protein Expression

Sf9 were grown to a cell density of $2\times10^7$ in serum-free TC100 medium and infected with the recombinant baculovirus with a multiplicity of infection (MOI) of 5. After infection the cells were grown for 5 to 7 days at 27° C. producing the VP1 protein encoded by the baculovirus. The produced protein is secreted into the expression medium. In the cell supernatant the secreted proteins self-assemble into VLPs.

b) Purification of VLPs from the Supernatant

Sf9 cells were separated from the supernatant by centrifugation for 5 min at 500×g. Cells were discarded and the supernatant was centrifuged a second time for 90 min at 5000×g in order to remove larger impurities.

The VLPs were then separated by ultracentrifugation. For this, 15 ml of clarified supernatant was loaded on 3 ml 40% sucrose.

Ultracentrifugation was performed in a Sorwall MX150 for 4 h at 100000×g and 4° C. In the centrifugation tube a pellet formed by the VLPs which was harvested. The VLP containing pellet was resuspended in Tris buffer (10 mM Tris, 150 mM NaCl, pH 7.5) The protein concentration of the resuspended VLPs was determined and adjusted to 0.5 μg/μl by the addition of Tris-Buffer.

Example 4: Production of VLPs Containing a VP1-Lyp1 Fusion Protein

FIG. 2 gives an overview of the production. In a first step, VP1 was produced as described in Example 3. VP1 with a Lyp-1 targeting peptide in the HI or DE loop were produced as described in Example 2.

The proteins were then mixed in a ratio of 5:1. Accordingly, 100 μl VP1 (500 ng/μl) were added to 200 μl VP1-HI-Loop-Lyp1 from *E. coli* (at a concentration of 50 ng/μl). The mixed VLPs were then disassembled by addition of 3 μl 0.5 M EDTA and 3 μl 1 M DTT at an incubation of 1 hour at 25° C. and 1,000 rpm shaking. The reassembly by dialysis against a calcium rich buffer then leads to the formation of mixed VP1 VLPs.

The sample was dialysed for 60 hours against 2 liters of Reassembly Buffer.

Reassembly Buffer
PBS
1 mM CaCl$_2$
1 mM MgCl$_2$ After 60 hours, the Reassembly Buffer was replaced by another 2 liters of the same buffer and the sample was dialysed for another 24 hours. Afterwards, the protein concentration in the sample was determined using the PIERCE 660 nM protein assay. Samples were analysed using SDS-PAGE and Western Blot Analysis. According to the same protocol VLPs containing VP1-DE-Loop-Lyp1 were produced.

Example 5: Targeting Test with VLPs Containing a VP1-Lyp1 Fusion Protein a) Labelling of VP1 with Fluorescent Dyes VP1 was produced using the established SF9/Baculo virus expression.

200 μl VP1 (0.5 mg/ml) from insect expression system were mixed with 10 μl of 0.2 M bicarbonate pH 9 and 0.5 μl 10 mM NHS-Ester of the fluorescent dye. The mixture was rotated at RT for 1 h before 1 μmol of ethanolamine was added to quench unreacted dye. Free dye was removed by dialysis against 2×1 Liter PBS containing 1 mM $CaCl_2$ and 1 mM $MgCl_2$ 24 h each.

b) Production of VLPs with VP1-Lyp1 Fusion Proteins and Dye Labelled VP1

The following VLPs assembled by VP1-Lyp1 fusion proteins and dye labelled VP1 were produced according to the protocol in Example 3.

i) VLP with VP1-DE-Loop-Lyp1 and VP1-FITC
ii) VLP with VP1-HI-Loop-Lyp1 and VP1-FITC
iii) VLP with VP1-DE-Loop-Lyp1 and VP1-Atto488
iv) VLP with VP1-HI-Loop-Lyp1 and VP1-Atto488
v) VLP with VP1-DE-Loop-Lyp1 and VP1-Atto647
vi) VLP with VP1-HI-Loop-Lyp1 and VP1-Atto647 c) Treatment of Cancer Cells Exhibiting p32 with the VLPs

The cancer cell line MDA-MB-231 (ATCC® HTB-26™) was applied into a 12-well plate with a cell number of about 200.000 cells per well. The cells are incubated at 37° C. and 5% $CO_2$ in 2 ml of the culture medium DMEM. After 20 h of incubation 4 μg of a VLP construct as defined in i) to vi) was added in the culture medium and the cells were incubated for another 4 h at 37° C. and 5% $CO_2$.

d) Flow Cytometry

After incubation with the VLP the culture medium was removed and the cells were washed by addition and subsequent removal of 2 ml of ice cold PBS. In the following cells were dissociated from the surface of the bottom of the well by addition of 500 μl T/E solution. To the cells 2 ml of PBS+2% (w/w) fetal calve serum (FCS) were added and the cell suspension were centrifuged for 10 min at 250 g and 5° C. Afterwards the cells were washed three times with 2 ml of PBS+2% (w/w) FCS. The cell suspension were centrifuged for 10 min at 250 g and 4° C. and the resulting cell pellet suspended in 1 ml PBS with 1 μg/ml propidium iodide.

The results of the flow cytometry are shown in form of histograms in FIG. 3 *a*) to *c*). FIG. 3 shows histograms calculated from flow cytometry data obtained from MDA-MB-231 cells treated with VLPs. The histogram curves in FIG. 3 *a*) to *c*) correspond to treatments with the VLPs from VP1, VP1-DE-Loop-Lyp1 or VP1-HI-Loop-Lyp1. In addition, a histogram from a control sample of untreated cells is present. In the histograms the X-axis represents the intensity of the measured signal, the Y-axis the number of cells with the specific signal intensity. In all experiments the histograms of the cell treatment with VLPs containing VP1-DE-Loop-Lyp1 or VP1-HI-Loop-Lyp1 are shifted to the right as compared to the cell treatment with VLPs containing only wildtype VP1. Thus, a larger number of cells take up the VLPs containing VP1 proteins with the targeting peptide (Lyo-1 as targeting region) according to the invention. An explanation for the increased uptake is the interaction of the Lyp-1 targeting region with the cancer cells exhibiting p32.

The results of the experiment are additionally shown in FIG. 4 in form of a column diagram. In FIG. 4 each column represents the percentage of cells with a positive uptake of VLPs, identified by minimum signal strength. FIG. 4 shows that the number of cells with a positive uptake of VLPs is increased by about 20% in the experiments with VLPs containing VP1-DE-Loop-Lyp1 and VP1-HI-Loop-Lyp1 compared to VLPs from normal VP1.

Example 6: Clinically Relevant Breast Cancer Spheroid Model a) Cells

Three breast cancer cell lines purchased from ATCC were selected. These cell lines represent the most relevant breast cancer cohorts, are known to form compact spheroids and incorporate the Atto-488 labeled VLPs. Namely, SKBr-3, passage 12 represents Her2/neu positive breast cancers, MCF-7, passage 11 the hormone receptor positive tumors and Hs578T, passage 17 the triple negative carcinomas.

For the preparation of heterotypic breast cancer spheroids, organ specific breast cancer fibroblasts in an early passage (F4616a, passage 4) and PBMC from a healthy donor were used. The breast cancer cell lines were cultured according to the recommendations published by ATCC. The primary fibroblasts were cultured in DMEM/F12 medium substituted with 10% FCS. The PBMC were isolated from lithium heparinized whole blood according to standard procedure and freshly used for spheroid preparation.

b) Preparation of Heterotypic Breast Cancer Spheroids

For spheroid formation single cell suspension was obtained by trypsinization of the monolayer cultures. Cell vitality was determined by trypan blue exclusion test: SKBr-3 cells: 92.4%, MCF-7 cells: 94.8%, Hs578T cells: 93%, primary breast cancer fibroblasts: 96.6% and PBMC: 99.6%.

For the preparation of heterotypic breast cancer spheroids single cell suspensions were mixed in a ratio of cancer cells (2): fibroblasts (1): PBMC (1). In each 96-well 50.000 mixed suspension cells were given in a volume of 100 μl DMEM/F12 based cell culture medium. Compact spheroids were generated according to SpheroTec's 3D technology for 48 h.

c) VLP Samples and Incubation of the Heterotypic Breast Cancer Spheroids

Three different types of VLPs labelled with Atto-488 were used as follows: VP1, VP1-HI-Loop-linRGD (an epitope of three repetitive RGD motifs), and VP1-HI-Loop-cycRGD (a cyclic RGD motif as described above, i. e. the RGD motif is comprised in the targeting region of the fusion protein according to a first aspect of the invention). The heterotypic breast cancer spheroids were incubated with 20 μl from each VLP and the mock control (supernatant from untransfected host cells) for six hours. All incubations were performed in triplicates.

After 6 h incubation with the VLP samples the heterotypic breast cancer spheroids were fixed in 10% PBS buffered formalin. After dehydration the spheroids were embedded in paraffin blocks according to a standard pathologic protocol.

d) Detection of the Bio-Distribution of the VLP Samples

For fluorescence microscopy 3 μm sections were prepared from the paraffin blocks. After deparaffinization and rehydration of the spheroid sections, bio-distribution of the Atto-488 labelled VLP samples was documented photographically using fluorescence microscopy.

Figure 5:
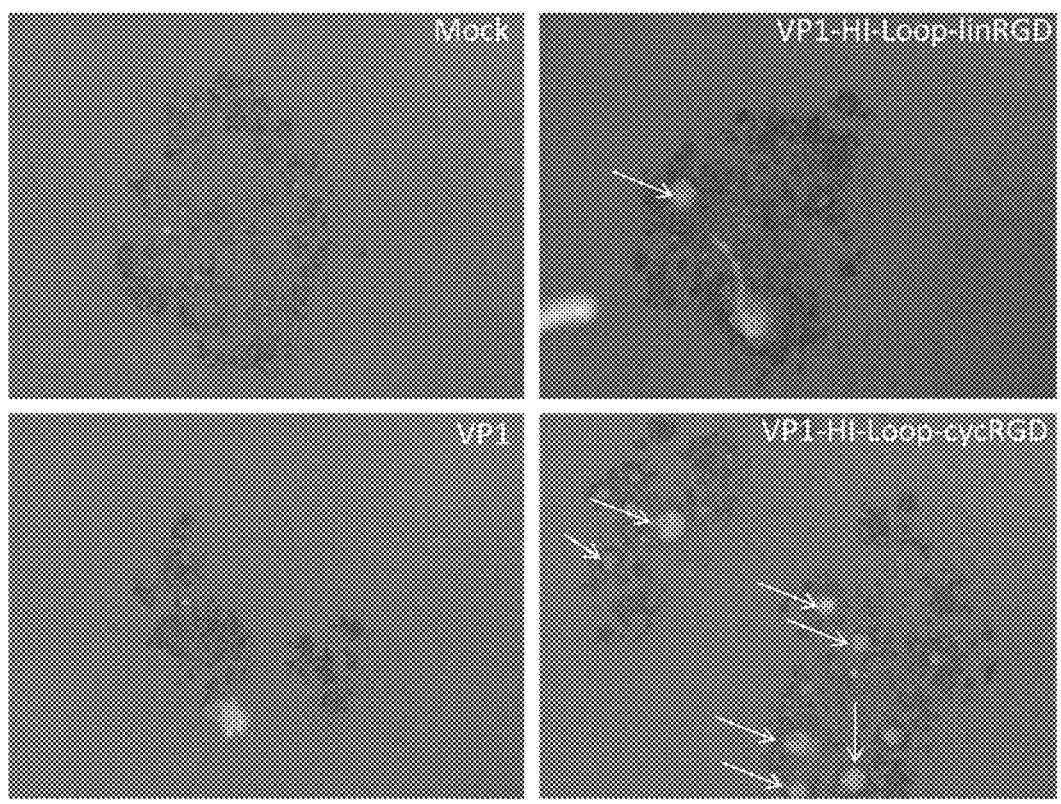

All tested VLP samples (see above) penetrated into the compact heterotypic breast cancer spheroid models within six (6) hours incubation time and showed an intracellular accumulation. Exemplarily, results are shown for the breast cancer cell line SKBr3. The architecture of the SKBr-3 spheroids was organized of aggregated tumor nodules. These tumor nodules mainly consisted of central fibroblasts surrounded by cancer cells. Leukocytes were found in both compartments. FIG. 5 shows the results of the breast cancer cell line SKBr3. Addition of the RGD motif leads to an increased VLP accumulation in the spheroid. The cyclic variant (VP1-HI-Loop-cycRGD) is much more effective than the linear one (VP1-HI-Loop-linRGD) demonstrating the potential of the strategy of cyclic peptide addition to VP1, i. e. of an exemplary fusion protein according to the present invention.

Figure 6:
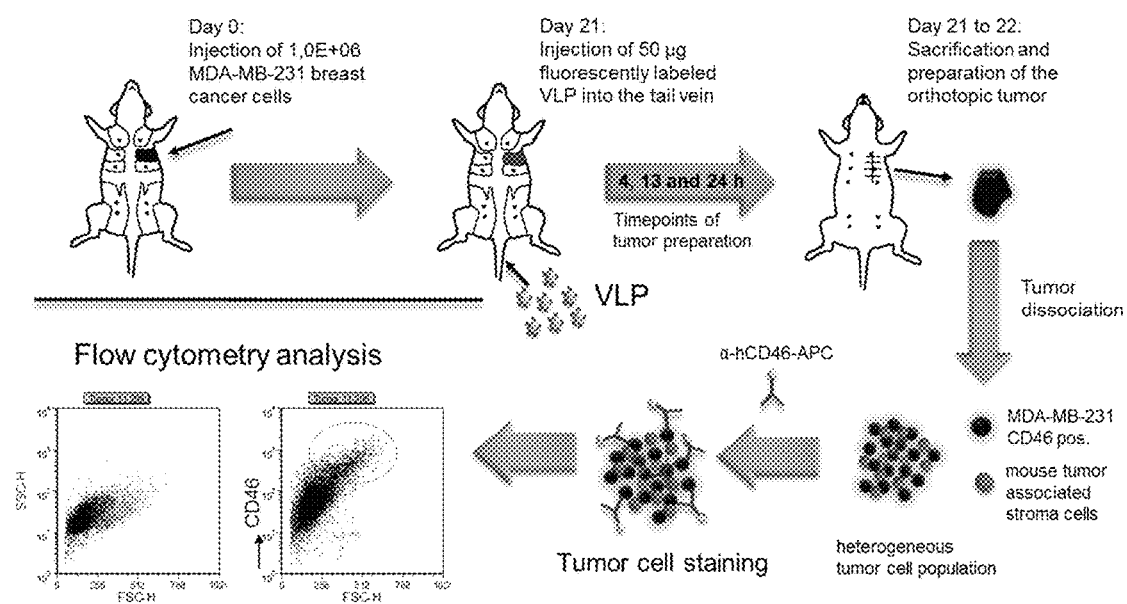

Example 7: Orthotopic Breast Cancer Tumor Model a) Study Design (See Also FIG. 6)

The study consisted of 2 experimental groups, each containing either 3 (animal control) or 9 (VP1-HI-Loop-Lyp1) female BALB/c nude mice after randomization. On day 0, 5×10$^6$ MDA-MB-231-Luc-Z1 tumor cells in 100 μl PBS:Matrigel were orthotopically implanted into 12 female BALB/c nude mice.

In the following, the growth of the orthotopically implanted primary tumors were determined twice weekly by caliper measurement. On day 20, tumor-bearing animals were randomized according to measured primary tumor volumes. On the following day (day 21), animals were once treated i.v. with 45 μg/animal (150 μl) of VP1-HI-Loop-Lyp1 or salt solution (animal control), respectively.

On days 21/22, 4 h, 13 h and finally 24 h after a single treatment, the respective animals were sacrificed and a necropsy performed.

At necropsy, animals were killed by cervical dislocation. Primary tumors were collected and wet weights and volumes determined. Primary tumor tissues were divided into two parts. One part was snap-frozen in liquid nitrogen and stored appropriately at −80° C., whereas the other part was analyzed by flow cytometry.

b) Flow Cytometry

One half of the primary tumors were chopped with a scalpel and digested 45-60 min at 37° C. for cell isolation (2 mg/ml collagenase (0.21 U/ml) and 25 μg/ml DNAse in PBS). Thereafter red blood cells were lysed and the remaining isolated cells stained with an anti-human CD46-APC antibody (BD Pharmingen, #564253). Flow cytometry analysis was performed using a BD-ExCalibur FACS analyzer. For each time point, an isotype control staining (mouse IgG2a, k-APC; BD-Pharmingen; #555576) was performed for one tumor sample.

Figure 7:
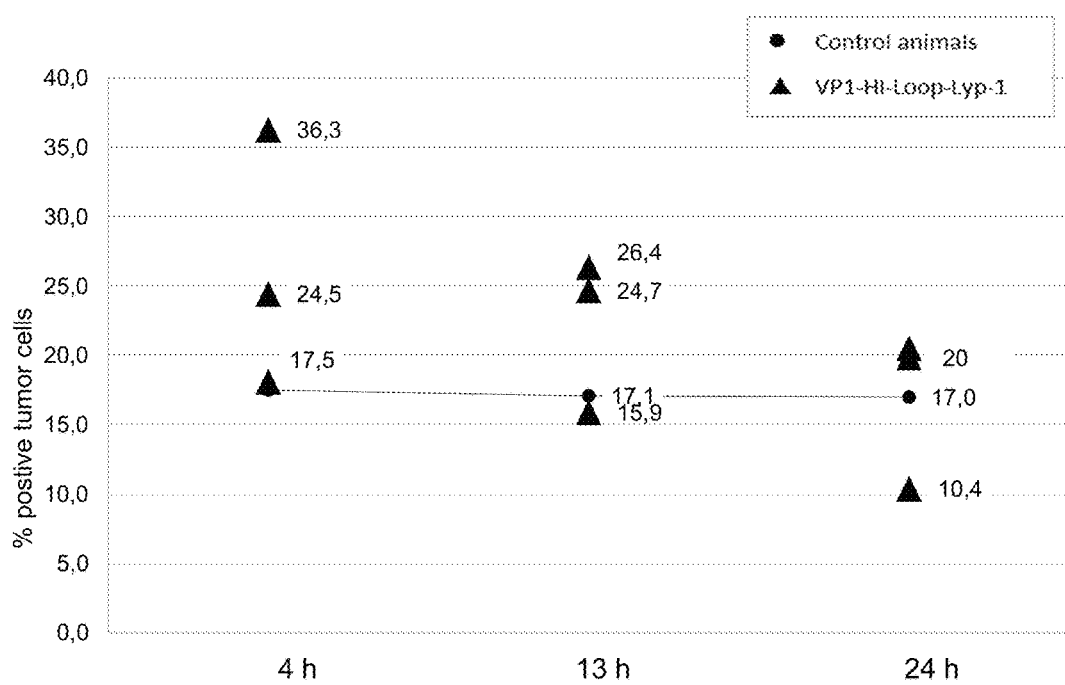

FIG. 7 demonstrates uptake of fluorescently labelled VLP-HI-Loop-Lyp1 in the tumors at each time point. At early time points uptake was more pronounced, pointing to a very fast kinetic. No fluorescence was found in mouse cells surrounding and penetrating the tumor.

Thus, targeting to tumor cells in vivo of VLP comprising a fusion protein according to a first aspect of the present invention has been demonstrated.

---

The invention claimed is:

1. A fusion protein comprising at least a first and a second peptide, wherein
   the second peptide comprises a targeting region and a first and a second interaction region,
   the first and the second interaction region form a stem and the targeting region forms a loop,
   the second peptide is located on the surface of the fusion protein,
   the second peptide comprises at least two interaction pairs, wherein an interaction pair is formed by an amino acid of the first interaction region and an amino acid of the second interaction region, at least one interaction pair is a covalent interaction pair in which the amino acids are covalently bound, and the first peptide is VP1 from JVC.

2. The fusion protein according to claim 1, wherein the covalent interaction pair is formed by a cysteine in the first interaction region and a cysteine in the second interaction region.

3. The fusion protein according to claim 1, wherein the amino acid sequence of the targeting region is selected from the group consisting of Lyp-1 (SEQ ID NO: 1), RGD (SEQ ID NO: 60), RGR, HER-2 binding peptide (SEQ ID NO: 2), CREKA peptide (SEQ ID NO: 3), NGR peptide CPP-2 (SEQ ID NO: 4), CPP-44 (SEQ ID NO: 5), F3 (SEQ ID NO: 6), RMS-P3 (SEQ ID NO: 7), F56 (SEQ ID NO: 8), LTVSPWY-peptide (SEQ ID NO: 9), and WNLPWYYS-VSPT-peptide (SEQ ID NO: 10).

4. A virus-like particle (VLP) comprising at least one fusion protein according to claim 1.

5. The VLP according to claim 4, wherein the second peptide is located on the outer surface of the VLP capsid.

6. The VLP according to claim 4, further comprising a second fusion protein comprising a VLP binding protein and an exogenous peptide.

7. The VLP according to claim 4, wherein the VLP comprises no cargo.

8. The VLP according to claim 4, wherein the VLP comprises a cargo selected from single-stranded or double-stranded DNA or RNA, preferably siRNA, oligopeptides, polypeptides, hormones, lipids, carbohydrates, other small organic compounds or mixtures thereof.

9. A method of treating a subject having a disease or diagnosing in a subject a disease, the method comprising administering the VLP according to claim 4.

10. A drug delivery system comprising the VLP according to claim 4.

11. A pharmaceutical composition comprising the VLP according to claim 4 and at least one pharmaceutically acceptable carrier.

12. An isolated polynucleotide comprising a nucleic acid sequence encoding a fusion protein according to any claims 1 to 3.

13. An expression vector comprising the polynucleotide according to claim 12.

14. A host cell comprising the expression vector according to claim 13.

15. A process of producing the VLP according to claim 4, the process comprising the steps of:

a) introducing an isolated polynucleotide comprising a nucleic acid encoding a fusion protein according to claim 1 into a host cell;

b) culturing the transformed host cell in a medium under conditions leading to a protein expression with the nucleic acid as a template;

c) isolating the expression product from the cell; and d) assembly of the expression product optionally with further viral proteins into the VLP.

16. The process according to claim 15, further comprising the steps:

e) disassembly of the VLP into pentamers;
f) mixture of the pentamers with wildtype VP1 pentamers; and
g) reassembly of VLPs from the pentamer mixture.

* * * * *